United States Patent [19]

Aiken et al.

[11] Patent Number: 5,192,798
[45] Date of Patent: Mar. 9, 1993

[54] LIPOPHILIC POLYAMINES USEFUL FOR TREATING HYPERCHOLESTEROLEMIA

[75] Inventors: James W. Aiken, Plainwell; Charles H. Spilman; Edward W. Thomas, both of Kalamazoo, all of Mich.

[73] Assignee: The Upjohn Company, Kalamazoo, Mich.

[21] Appl. No.: 566,441

[22] PCT Filed: Feb. 13, 1989

[86] PCT No.: PCT/US89/00490

§ 371 Date: Aug. 16, 1990

§ 102(e) Date: Aug. 16, 1990

Related U.S. Application Data

[63] Continuation-in-part of Ser. No. 158,213, Feb. 19, 1988, abandoned.

[51] Int. Cl.$^5$ .................... A61K 31/16; C07C 211/18
[52] U.S. Cl. .................... 514/462; 514/419; 514/529; 514/557; 514/613; 514/616; 514/859; 549/341; 458/303; 458/340; 560/125; 562/498; 562/507; 564/152; 564/191; 564/457; 564/461
[58] Field of Search ............... 549/341; 514/462, 519, 514/529, 557, 613, 616, 659; 558/303, 430; 560/125; 562/498, 507; 564/152, 191, 457, 461

[56] References Cited

U.S. PATENT DOCUMENTS

| | | | |
|---|---|---|---|
| 2,874,174 | 2/1959 | Huber | 260/404.5 |
| 3,291,808 | 12/1966 | Elslager | 260/326.85 |
| 3,734,953 | 5/1973 | Bernstein | 260/501.11 |
| 4,003,934 | 1/1977 | Grier | 260/586 G |
| 4,631,337 | 12/1986 | Tomalia | 528/391 |

FOREIGN PATENT DOCUMENTS

| | | |
|---|---|---|
| 2039214 | 2/1971 | Fed. Rep. of Germany . |
| 2624528 | 12/1977 | Fed. Rep. of Germany . |
| 1065248 | 5/1954 | France . |
| 61-146265 | 7/1986 | Japan . |
| WO87/0237 | 4/1989 | PCT Int'l Appl. . |

Primary Examiner—Richard L. Raymond
Attorney, Agent, or Firm—Martha A. Gammill; Thomas A. Wootton

[57] ABSTRACT

This invention relates to novel lipophilic polyamines of formula I, the method of using these compounds to treat hypercholesterolemia, and intermediates thereto.

$$Z_1-(CH_2)_n-Y_1-X_1-R_1 \qquad I$$

10 Claims, No Drawings

LIPOPHILIC POLYAMINES USEFUL FOR TREATING HYPERCHOLESTEROLEMIA

CROSS REFERENCE TO RELATED APPLICATIONS

This application is a continuation of copending International Application PCT/US89/00490, filed Feb. 2, 1989, which designated the U.S.; which is a continuation-in-part of U.S. application Ser. No. 07/158,213 filed Feb. 19, 1988, now abandoned.

FIELD OF THE INVENTION

This invention includes novel lipophilic polyamines which are useful for treating hypercholesterolemia and intermediates thereto. Background of the Invention Cholesterol is probably the sole precursor of bile acids. During normal digestion, bile acids are secreted into the intestines. A major portion of the bile acid is absorbed from the intestinal tract and returned to the liver via the enterohepatic circulation system. Only very small amounts of bile acids are found in normal serum. Polymeric anion exchange resins are known to combine with the bile acids in the intestine to form an insoluble complex which is excreted in the feces. This results in partial removal of bile acids from the enterohepatic circulation by preventing their reabsorption. The increased fecal loss of bile acids leads to an increased oxidation of cholesterol to bile acids, a decrease in beta lipoprotein or low density lipoprotein plasma levels and a decrease in plasma cholesterol levels. Although excretion of bile acids produces an increase in hepatic synthesis of cholesterol, plasma cholesterol falls. These anion exchange resins are not systemically absorbed or digested although large quantities, up to 54 grams of the formulated resin per day for cholestyramine resin powder, are needed. These resins are not water soluble but are typically administered as an aqueous suspension.

Colestipol-niacin therapy has recently been shown to significantly increase the regression of atherosclerosis in drug-treated subjects. D. H. Blankenhorn et al., JAMA, 1987, 257:3233-3240. Others have found cholestyramine reduces the incidence of coronary heart disease in treated patients. Lipid Research Clinics Program, JAMA. 1984 251:351-364. With the positive effects of resins on coronary heart disease, one must balance the sometimes poor patient compliance. Therefore the medical community has recognized the need for new effective drugs of this type. S. M. Grundy, "Drugs Affecting Lipid Metabolism"; R. Paoletti Ed., Springer Verlag: Berlin 1987, pp. 34–41. Information Disclosure Some of the amino substituted hydrocarbons used to practice this invention are claimed in International Patent Application PCT/US86/02116 which has an International Publication Date of Apr. 23, 1987. The International Application teaches these compounds are useful to treat phospholipid mediated conditions and diabetes.

The following are references to polyamine compounds similar to the compounds described herein, but not for the use of our invention.

CA 88:106267Z (German Patent, DE 2624528) discloses 1,2-Ethanedicimine, N-[2-(dimethylamino)ethyl]-N',N'-bis[2-[[2-(dimethylamino)ethyl]methylamino]ethyl]-N-methyl-, useful as polyurethane foam materials.

CA 105:197229X (Japanese Patent, J61146265) discloses Ethanaminium, N,N-bis(2-amino-ethyl)-N-(carboxymethyl)-2-(dodecylamino)chloride, useful as an antimicrobial agent.

CA 74:99664g (German Patent, DE 2039214 and U.S. Pat. No. 3,734,953) disclose Isophthalamic acid, N,N',N''-(nitrilotriethylene)tris[5-nitro-, trimethyl ester, useful as a radiopaque agent.

CA87:22564k (U.S. Pat. No. 4.003.934) discloses 1,2-Ethanediamine, N,N-bis(2-aminoethyl)-N'[2-(3,3-dimethylbicyclo[2.2.1]hept-2-yl)-1 [2-(3,3-dimethylbicyclo[2.2.1]hept-2-yl)ethyl]propyl]tetrahydrochloride, useful as an antimicrobial agent.

CA67:21731n (U.S. Pat. No. 3,291,808) discloses N-(dialkylaminoalkyl)-1,4-naphthalenediamines having useful antiparasitic properties.

CA107:40601f (U.S. Pat. No. 4.631 337) discloses hydrolyticallystable dense star polyamines, which are useful as calibration standards, high efficiency proton scavengers and in making size selective membranes.

CA54:26191g (U.S. Pat. No. 2.874.174) discloses alkyl amides of N,N,N-tris(aminoalkyl)amines which are useful as binding agents for asphalt pavements.

SUMMARY OF THE INVENTION

A compound of the formula I
wherein $Z_1$ is
   (a) $-C_3-C_{20}$-cycloalkyl substituted with zero or one $=O, C(O)OR_{11}, -C(O)NH_2, -CH=CH_2$, or ethylene ketal;
   (b) $-C_3-C_{20}$-alkyl substituted with zero or one $=O, -C(O)OR_{11}, C(O)NH_2, -CH=CH_2$, or ethylene ketal;
   (c) -alkyl($C_1-C_{12}$)-cycloalkyl($C_3-C_8$);
   (d) -benzyl substituted with zero, one, or two $=O, -C(O)OR_{11}, C(O)NH_2, -CH=CH_2, -CF_3$, -phenyl or -benzyl-oxy; or
   (e) -phenyl substituted with zero, one or two $-C(O)OR_{11}, -C(O)NH_2, -CH=CH_2, -CF_3$, -phenyl or benzyl-oxy;
wherein $Y_1$ is
   (a) $-C(O)-$, or
   (b) absent;
wherein $X_1$ is
   (a) $-NR_2-$,
   (b) $-NR_2R_3$, or
   (c) $-N(R_2)_2R_3X_4$;
wherein $X_4$ is a pharmaceutically acceptable anion;
wherein $R_1$ is
   (a) $-H$,
   (b) $-C_1-C_4$alkyl,
   (c) -benzyl,
   (d) $-(CH_2)_p-N(R_4)(R_5)$,
   (e) $-(CH_2)_p-N(R_4)-Y_1-R_5$, or
   (f) when $X_1$ is $-NR_2R_3$ or $-N(R_2)_2R_3X_4$, $R_1$ is absent;
wherein $R_2$ is
   (a) $-H$,
   (b) $-C_1-C_6$alkyl,
   (c) $-(CH_2)_m-N(R_4)(R_5)$,
   (d) $-(CH_2)_m-N(R_4)-Y_1-R_5$,
   (e) $-(CH_2)_m-O-(CH_2)_m-N(R_4)(R_5)$, or
   (f) $-(CH_2)_m-NH-C(NH)-NH_2$;
or when $X_1$ is $-NR_2-$, wherein $R_1$ and $R_2$ taken together can be $-(CH_2)_qX_3-(CH_2)_q-$;
wherein $R_3$ is
   (a) $-CH_3$, or
   (b) $=O$;
wherein $R_4$ is
   (a) $-H$, (b) —$C_1$—$C_6$alkyl
(c) -benzyl,
(d) —phenyl,
(e) —$(CH_2)_q$—$N(R_6)(R_7)$,
(f) —$(CH_2)_q$—$N(R_6)$—$Y_1$—$R_7$, or
(g) —$(CH_2)_q N(R_6)_3 X_4$;

wherein $R_5$ is
(a) —H,
(b) —$C_1$—$C_6$alkyl,
(c) —$(CH_2)_r$—$N(R_8)(R_9)$,
(d) —$(CH_2)_r$—$N(R_8)$—$Y_1$—$R_9$, or
(e) —$(CH_2)_r$—$N(R_8)_3 X_4$;

or wherein $R_4$ and $R_5$ taken together are —$(CH_2)_q$—$X_2$—$(CH_2)_q$—;

wherein $R_6$, $R_7$, $R_8$, or $R_9$ is each independently
(a) —H,
(b) —$C_3$—$C_{20}$cycloalkyl substituted with zero or one =O, $C(0)OR_{11}$, —$C(0)NH_2$, $CH=CH_2$, or ethylene ketal;
(c) —$C_3$—$C_{20}$alkyl substituted with zero or one =O, —$C(0)OR_{11}$, $C(0)NH_2$, —$CH=CH_2$, ethylene ketal or $C\equiv N$;
(d) -alkyl ($C_1$—$C_{12}$)—cycloalkyl ($C_3$—$C_8$),
(e) -benzyl substituted with zero, one, or two =O, —$C(0)OR_{11}$, $C(0)NH_2$, —$CH=CH_2$, —$CF_3$, —phenyl or benzyl—oxy;
(f) —phenyl substituted with zero one or two —$C(0)OR_{11}$, $C(0)NH_2$, —$CH=CH_2$, —$CF_3$, —phenyl or -benzyl—oxy;
(g) —$(CH_2)_s$—$N(R_{10}(R_{11})$;
(h) —$(CH_2)_s$—$N(R_{10})$—$Y_1$—$R_{11}$;
(i) amino acid residue, or
(j) —$(CH_2)_s$—Het;

or wherein $R_6$ and $R_7$ taken together are —$(CH_2)_q$—$X_2$ $(CH_2)_q$—;
or wherein $R_8$ and $R_9$ taken together are —$(CH_2)_q X_2$—$(CH_2)_q$—; wherein $R_{10}$ or $R_{11}$ is each independently
(a) —H,
(b) —$C_1$—$C_6$alkyl, or
(c) —$(CH_2)_n$—$NH_2$;

or wherein $R_{10}$ and $R_{11}$ taken together are —$(CH_2)_q$—$X_2$ $(CH_2)_q$;

wherein $X_2$ is
(a) —O—,
(b) —NH—,
(c) —$N(CH_3)$ or
(d) —N—$(CH_2)_q$—$NH_2$;

wherein $X_3$ is
(a) —O—,
(b) —S—,
(c) —NH—, or
(d) —$N(CH_3)$—;

wherein —Het is a 5- or 6-membered saturated or unsaturated ring containing from one to three heteroatoms selected from the group consisting of nitrogen oxygen, and sulfur; and including any group in which any of the above heterocyclic rings is fused to a benzene ring, which heterocyclic moiety is substituted with zero to three of the following:
(i) $C_1$-$C_6$alkyl,
(ii) hydroxy,
(iii) trifluoromethyl,
(iv) $C_1$-$C_4$alkoxy,
(v) halo,
(vi) phenyl,
(vii) phenyl $C_1$-$C_4$alkyl-,
(viii) amino,
(ix) mono— or di-($C_1$-$C_4$alkyl)amino, and
(x) $C_1$-$C_5$alkanoyl;

wherein n is zero to five, inclusive; wherein m, p, q, r or s is each independently one to ten, inclusive; with the provisos that:

1) If $Z_1$ is $C_8$-$C_{20}$-cycloalkyl, then one of the following must occur:
 a) $R_1$ is other than —H, $C_1$—$C_4$alkyl, or benzyl;
 b) $R_2$ is other than —H, —$C_1$—$C_6$alkyl or —$(CH_2)_m$—NH—$C(NH)$—$NH_2$;
 c) when $R_1$ is —$(CH_2)_p$—$N(R_4)(R_5)$ or when $R_2$ is -$(CH_2)_m$—$N(R_4)(R_5)$ or —$(CH_2)_m$—O—$(CH_2)_m$—$N(R_4)(R_5)$, then $R_4$ is other than —H,$C_1$—$C_6$alkyl, -benzyl, or —phenyl and $R_5$ is other than —H or —$C_1$—$C_6$alkyl;
 d) when $R_4$ is —$(CH_2)_q$—$N(R_6)(R_7)$, then $R_6$ and $R_7$ are other than —H, —$(CH_2)_3$—$NH_2$;
 e) $R_1$ and $R_2$ are not taken together; or
 f) $R_4$ and $R_5$ are not taken together; and
2) If $Z_1$ is $C_{10}$-$C_{20}$alkyl, then $Y_1$ is absent.

A compound selected from the group consisting of:
1,2-Ethanediamine, N,N-bis(2-aminoethyl)-N'-cyclododecyl;
1,2-Ethanediamine, N-(2-aminoethyl)-N'-cyclododecyl;
1,2-Ethanediamine, N,N-bis(2-aminoethyl)-N'-cyclohexyl-;
1,3-Propanediamine, N,N''-[2-(cyclododecylamino)ethylimino-di2,1-ethanediyl]-bis-;
1,2-Ethanediamine, N-cyclododecyl-N',N'-bis-2-(dimethylamino)-ethyl-N-methyl-;
Octadecanamide, N-[2[bis(2-aminoethyl)amino]ethyl]-; and
Octadecacamide, N,N'-[[(2-aminoethyl)imino]di-2,1-ethanediyl]-bis-.

A method of treating hypercholesterolemia in an affected patient which comprises administering to said patient an effective amount for reducing serum cholesterol in said patient of a member selected from the group consisting of the free bases and pharmaceutically acceptable salts of a compound of formula I wherein $Z_1$ is
(a) —$C_3$—$C_{20}$-cycloalkyl substituted with zero or one =O,$C(0)OR_{11}$, —$C(0)NH_2$, —$CH=CH_2$, or ethylene ketal;
(b) —$C_3$—$C_{20}$-alkyl substituted with zero or one =O, —$C(0)OR_{11}$,$(0)NH_2$, —$CH=CH_2$, or ethylene ketal;
(c) -alkyl($C_1$—$C_{12}$)-cycloalkyl($C_3$-$C_8$);
(d) -benzyl substituted with zero, one, or two —$C(0)OR_{11}$,$C(0)NH_2$, —$CH=CH_2$, —$CF_3$, —phenyl or —benzyl—oxy; or
(e) -phenyl substituted with zero, one or two —$C(0)OR_{11}$,$C(0)NH_2$, —$CH=CH_2$, —$CF_3$, —phenyl or —benzyl—oxy; or
(f) a steroid of formula II;

wherein $A_1$ is
(a) —$(CH_2)_4$—,
(b) —$CH_2$—$CH_2$—$C(0)$—$CH$—, or
(c) —$CH_2$—$CH_2$—$CH(E_1)$—$CH_2$—;

wherein $D_1$ is
(a) -hydrogen, or
(b) -methyl;

wherein $E_1$ is
(a) -hydrogen, or
(b) —$OF_1$;

wherein $F_1$ is
(a) —H,
(b) —$C_1$—$C_3$alkyl, or
(c) —benzyl;

wherein $Y_1$ is
  (a) —C(O)—, or
  (b) absent;
wherein $X_1$ is
  (a) —NR$_2$—,
  (b) —NR$_2$R$_3$, or
  (c) —N(R$_2$)$_2$R$_3$X$_4$;
wherein $X_4$ is a pharmaceutically acceptable anion;
wherein $R_1$ is
  (a) —H,
  (b) —C$_1$—C$_4$alkyl,
  (c) —benzyl,
  (d) —(CH$_2$)$_p$—N(R$_4$)(R$_5$),
  (e) —(CH$_2$)$_p$—N(R$_4$)—Y$_1$—R$_5$, or
  (f) when $X_1$ is —NR$_2$R$_3$ or —N(R$_2$)$_2$R$_3$X$_4$, $R_1$ is absent;
wherein $R_2$ is
  (a) —H,
  (b) —C$_1$—C$_6$alkyl,
  (c) —(CH$_2$)$_m$—N(R$_4$)(R$_5$),
  (d) —(CH$_2$)$_m$—N(R$_4$)—Y$_1$—R$_5$,
  (e) —(CH$_2$)$_m$—O—(CH$_2$)$_m$—N(R$_4$)(R$_5$), or
  (f) —(CH$_2$)$_m$—NH—C(NH)—NH$_2$;
or when $X_1$ is —NR$_2$—, wherein $R_1$ and $R_2$ taken together can be —(CH$_2$)qX$_3$—(CH$_2$)$_q$—;
wherein $R_3$ is
  (a) —CH$_3$, or
  (b) =O;
wherein $R_4$ is
  (a) —H,
  (b) —C$_1$—C$_6$alkyl,
  (c) —benzyl,
  (d) —phenyl,
  (e) —(CH$_2$)$_q$—N(R$_6$)(R$_7$),
  (f) —(CH$_2$)$_q$—N(R$_6$)Y$_1$R$_7$, or
  (g) —(CH$_2$)$_q$—N(R$_6$)$_3$X$_4$;
wherein $R_5$ is
  (a) —H,
  (b) —C$_1$—C$_6$alkyl,
  (c) —(CH$_2$)$_r$—N(R$_8$)(R$_9$),
  (d) —(CH$_2$)$_r$—N(R$_8$)—Y$_1$—R$_9$, or
  (e) —(CH$_2$)$_r$—N(R$_8$)$_3$X$_4$;
or wherein $R_4$ and $R_5$ taken together are —(CH$_2$)$_q$—X$_2$—(CH$_2$)$_q$; wherein $R_6$, $R_7$, $R_8$, or $R_9$ is each independently
  (a) —H,
  (b) —C$_3$—C$_{20}$, cycloalkyl substituted with zero or one =O C(O)OR$_{11}$, —C(O)NH$_2$, —CH=CH$_2$, or ethylene ketal;
  (c) —C$_3$—C$_{20}$alkyl substituted with zero or one =O, —C(O)OR$_{11}$,C(O)NH$_2$, —CH=CH$_2$, ethylene ketal or C≡N;
  (d) -alkyl (C$_1$-C$_{12}$)—cycloalkyl (C$_3$—C$_8$),
  (e) -benzyl substituted with zero, one, or two —C(O)OR$_{11}$,C(O)NH$_2$, —CH=CH$_2$, —CF$_3$, -phenyl or —benzyl-oxy..
  (f) -phenyl substituted with zero, one, or two —C(O)OR$_{11}$,C(O)NH$_2$, —CH=CH$_2$, CF$_3$, -phenyl or -benzyl-oxy;
  (g) —(CH$_2$)$_s$—N(R$_{10}$)(R$_{11}$;
  (h) —(CH$_2$)$_s$—N(R$_{10}$)—Y$_1$—R$_{11}$;
  (i) amino acid residue; or
  (j) —(CH$_2$)$_s$—Het;
or wherein $R_6$ and $R_7$ taken together are —(CH$_2$)$_q$—X$_2$—(CH$_2$)$_q$—;
or wherein $R_8$ and $R_9$ taken together are —(CH$_2$)$_q$—X$_2$—(CH$_2$)$_q$—;
wherein $R_{10}$ or $R_{11}$ is each independently
  (a) —H,
  (b) —C$_1$—C$_6$alkyl, or
  (c) —(CH$_2$)$_n$—NH$_2$;
or wherein $R_{10}$ and $R_{11}$ taken together are —(CH$_2$)$_q$—X$_2$—(CH$_2$)$_q$;
wherein $X_2$ is
  (a) —O—,
  (b) —NH—,
  (c) —N(CH$_3$)—, or
  (d) —N—(CH$_2$)$_q$—NH$_2$;
wherein $X_3$ is
  (a) —O—,
  (b) —S—,
  (c) —NH—, or
  (d) —N(CH$_3$)—;
wherein -Het is a 5- or 6- membered saturated or unsaturated ring containing from one to three heteroatoms selected from the group consisting of nitrogen, oxygen, and sulfur; and including any group in which any of the above heterocyclic rings is fused to a benzene ring, which heterocyclic moiety is substituted with zero to three of the following:
  (i) C$_1$-C$_6$alkyl,
  (ii) hydroxy,
  (iii) trifluoromethyl,
  (iv) C$_1$-C$_4$alkoxy,
  (v) halo,
  (vi) phenyl,
  (vii) phenyl C$_1$-C$_4$alkyl-,
  (viii) amino,
  (ix) mono- or di-(C$_1$-C$_4$alkyl)amino, and
  (x) C$_1$-C$_5$alkanoyl;
wherein n is zero to five, inclusive; wherein m, p, q, r or s is each independently one to ten, inclusive; provided that the compound is other than:
  1,2-Ethanediamine, N,N-bis(2-aminoethyl)-N'-cyclohexyl-;
  1,2-Ethanediamine, N,N-bis(2-aminoethyl)-N'-1,4-dioxaspiro-4.5-dec-8-yl-;
  1,2-Ethanediamine, N,N-bis-2-(1,4-dioxaspiro-4.5-dec-8-ylamino)-ethyl-;
  N,N-Bis-(2-aminoethyl)-N'-phenylmethyl-1,2-ethanediamine;
  N-2-aminoethyl)-N'-(phenylmethyl)-N-(2-((phenylmethyl)amino)ethyl); or
  N[[2-(-Bis(2-sminoethyl)amino]ethyl]benzamide.

DETAILED DESCRIPTION OF THE INVENTION

By "amino acid residue" is meant the naturally-occurring amino acids such as: glycine, alanine, valine, leucine, isoleucine, phenylalanine, lysine, proline, tryptophan, methionine, serine, threonine, cysteine, tyrosine asparagine, glutamine aspartic acid, glutamic acid, arginine, ornithine, and histidine, and synthetic derivatives thereof. These compounds may be in L or D configuration and are well known and readily available to those skilled in the art.

Unless otherwise indicated, in the above description and throughout this document: (a) the parenthetical term (C$_n$-C$_m$) is inclusive such that a compound of (C$_1$-C$_4$) would include compounds of 1, 2, 3 and 4 carbons and their isomeric forms.

The scope of this invention includes the pharmacologically acceptable acid salts of the disclosed compounds. Acid salts are formed by reacting the compounds described herein with the appropriate acid in a suitable solvent. Suitable acids for this purpose include hydrochloric, sulfuric, phosphoric hydrobromic, hydroiodic, acetic, lactic, citric, succinic, benzoic, salicylic, palmoic, cyclohexansulfamic, methanesulfonic, naphthalenesulfonic, p-toluenesulfonic, maleic, fumaric, or oxalic.

Some of the compounds used to practice this invention are prepared by the methods and processes taught in U.S. Pat. No. 4,917,826, issued Apr. 17, 1990. This application is herein incorporated by reference. The methods and processes used to prepare amino cyclic hydrocarbons are described on pages 18 to 24 and the related charts and specific examples are described on pages 28 to 114.

Charts A, G, H, & I (Generic Charts)

The compounds A-3, A-4 and A-5 are made from commercially available ketones or aldehydes A-1 (or readily synthesized ketones or aldehydes) and commercially available amines, by reductive amination methods (See R. F. Borch, M. D. Berstein, H. D. Durst, JACS, 93:2897-2904, 1971; and J. H. Billman, and A. O. Diesing, J.O.C., 22:1068-1070, 1957).

The compounds G-3, G-5 and G-7 are made from esters or activated esters G-1, G-4 and G-6, and amines G-2, using the procedures set forth in A. L. J. Bechmith, in "The Chemistry of Amides"; J. Zuhicky, Ed., Interscience, New York, Chapter 2, 1970.

The compound A-5 is elaborated by reacting free amines I-1 (A-5) and H-1 (A-5) with unsaturated esters J-2 or nitriles H-2 for chain extended compounds I-3 and H-3, respectively. The intermediate H-3 is then reduced to the corresponding final amine H-4. The intermediate I-3 is further reacted with amine I-4 to yield the final product I-5. I-5 is reduced to yield another final product I-1.6.

Chart B (Scheme 1)

While employing commercially available B-1 and only 1.2 equivalents of amine B-2, B-3 and dialkylated amine B-4 are isolated. These polar compounds are separated by chromatography on commercially available silica gel when eluting with chloroform/methanol/ammonium hydroxide.

Chart B (Scheme 2)

For the formation of compounds B-6, 2 equivalents of amine (B-2) to ketone (B-5) is optimum for the formation of mono-adducts. When 2 equivalents of amine B-2 are reacted with one equivalent of ketone B-5, a statistical 1:2:1 ratio of B-6;B-7;B-8 are formed. Further treatment of amine B-2 with 4 equivalents of ketone B-5 affords the tris-adduct B-8, with no trace of monoadduct B-6.

Chart B (Scheme 3)

For the formation of compound B-10, 2 equivalents of amine to ketone is optimum for the formation of mono-adducts.

Chart B (Schemes 4, 5 and 6)

Additional analogs B-12, B-13, B-15, B-16, and B-18 are also synthesized by this method. The rings of B-15 and B-16 contain functional groups. The compound B-14 and B-17 are commercially available.

Chart B (Schemes 7, 8)

Two open-chain analogs, B-20 and B-22, also are produced by this methods.

Chart C
(Reductive amination of aldehydes)

The compound C-3, wherein R is pentadecyl, is formed by hydrogenating the imine derived from hexadecyl aldehyde and the amine C-2. W. H. Emerson, Org. React. 1948, 4, 174-255. For the synthesis of imines see, S. Dayagi and Y. Degani, "The Chemistry and CarbonNitrogen Double Bond", S. Patai, Ed., Interscience: New York, 1970: Chapter 2. Other adducts as listed in the Table for Chart C are synthesized by the same method. The compound C-3 wherein R is (BnO)$_2$-phenyl- is produced by reducing the intermediate imine with sodium borohydride in methanol. J. H. Billman and A. C. Diesing, J. Org. Chem. 1957, 22, 1068-1070.

Chart D (Scheme 1)

Amide derivatives of simple amines are readily available by a number of methods. A. L. J. Beckwith, in "The Chemistry of Amides"; J. Zubicky, Ed., Interscience: New York, 1970; Chapter 2. Treatment of ester D-1 on a steam bath with amine D-2 yields the amide D-3 and the diamide D-4, that are separated by column chromatography.

Chart D (Schemes 1 and 3)

Other acylating agents such as acid chlorides D-5 and D-7 when treated with amine D-2, afford none of the monoacylated material.

Chart D (Schemes 4 and 5)

A method found to produce at least a statistical product distribution from polyamines consists of increasing the reaction dilution and decreasing the reactivity of the acylating agent. A. R. Jacobson, et a., J. Org. Chem. 1987, 52, 2592-2594. The compound D-9 and diamine D-10 yield mainly D-11 and some diacylated D-12. Anhydride D-9 and amine D-2 form the monoacylated compound D-13 and diacylated D-14.

Chart E (Schemes 1 and 2)

[Amine portion modification] [Amine chain extension] Selective Michael addition of 2 equivalents of acrylonitrile of E-2 to the primary amines of E-1, prepared as the compound B-16 in Chart B, form the compound E-3. Reduction of the nitriles with lithium aluminum hydride (LAH) produces the hexamine E-4. In a similar fashion, methyl acrylate E-5 and amine E-1 produce the diester E-6. Following chemistry developed to produce starburst or arborol compounds (D. A. Tomalia, et al., Polymer Journal 1985, 17, 117-132; G. R. Newkome, et al., J. Am. Chem. Soc. 1986, 108, 849-850.), the diester E-6 is treated with excess ethylenediamine to yield the amine extended analog E-7.

Chart F (Schemes 1, 2 and 3)

The Eschweiler-Clark reaction affords pentaalkylated amine F-3. S. H. Pine and B. L. Sanchez, J. Org. Chem. 1971, 36, 829-832; M. L. Moore, Org. React. 1949, 5, 301-330. The two less hindered amines of F-3 are selectively alkylated with 2 equivalents of methyl iodide to form F-4. The Eschweiler-Clark reaction is also employed to produce analog F-6.

Biological studies demonstrate the utility of this invention. Male SEA Japanese quail, approximately four to six weeks of age, were reared at Miles Quail Farm, Gobles, Mich. Prior to drug testing, birds were randomly distributed into 10-15 groups of 10 quail each. They were housed individually in 10 cage units and fed a commercial diet (Purina Game Bird Layena, Ralston Purina Co., St. Louis, Mo.) mixed with 0.5% cholesterol and 1% peanut oil (diet D1) for 14 days. Compounds were mixed into 2.4 kg of the diet by a special mixer (Hobart A-200) for 20 minutes. Control groups received diet D1 alone, and positive control groups received diet D1 mixed with colestipol hydrochloride) at an amount to provide a dose of 750 mg/kg/day.

After two weeks on the diets, each bird was bled from the right jugular vein and serum samples were obtained after low speed centrifugation. Food intake was determined for each group by subtracting the weight of diet remaining at the end of the experiment from the weight of the starting diet.

Normal male rats, UPJ:TUC(SD)spf, weighing 100-110 grams were evenly distributed by weight into groups of ten. The animals were housed in stainless steel cages with five rats in each cage. Food and water were allowed ad libitum. The rats were placed on a defined diet containing 1% (wt/wt) cholesterol. The diet was in powder form and was presented to the rats in feed jars fitted with stainless steel guards to prevent loss of feed. Compounds to be tested were mixed into this diet using a Hobart A-200 mixer. Colestipol hydrochlorideadministered at daily doses of 500 and/or 1000 mg/kg is used as the positive control in this assay. After seven days on the diet with or without test compound, the rats were anesthetized with Cyclopal sodium and bled from the right jugular vein. Serum samples were obtained after low speed centrifugation.

Beta- and alpha-lipoproteins were isolated from individual serum samples using PEG-8000 and glycine buffer, pH 9. Three hundred microliters of serum were mixed with 300 microliters of solution A (20 gram of PEG-8000+100 ml of glycine buffer, pH 9) using a Micromedic automatic pipette. Samples were allowed to stand at room temperature for 10 minutes and were then centrifuged for 20 minutes at 2000 × g at 4° C. The beta-lipoprotein pellet was dissolved in 300 microliters of solution B (10 ml Triton X-100+1000 ml Milli Q water). Cholesterol, triglycerides and total protein in alpha- and beta-lipoproteins were measured using the Demand Autoanalyzer Aystem Model AU 500 (Cooper Biomedical Inc.) and Worthington Demand Enzymatic reagents.

All data were statistically analyzed using a one-way classification design. All values were transformed to logarithms to achieve more homogeneous within-group variances. The mean response for each test compound was compared with the mean observed in the animals fed the cholesterol-containing diet alone by the LSD test. The compound, N,N-Bis-2-(cyclododecylamino)ethyl-1,2-ethanediamine, is about 15 times more potent than colestipol hydrochloride; the effect of 50 mg/kg/day was similar to the effect of 750 mg/kg/day of colestipol hydrochloride.

The results of studies performed using SEA quail are shown in Table 1. The compound N,N-bis(2-aminoethyl)-N'-cyclopentadecyl-1,2-ethanediamine administered at 150 mg/kg/day, is about fifteen times more potent than colestipol hydrochloride; the effect of 150 mg/kg/-day of N,N-bis(2-aminoethyl)-N'-cyclopentadecyl-1,2-ethanediamine was similar to the effect of 2250 mg/kg/day colestipol hydrochloride.

The results of studies performed in cholesterol-fed rats are shown in Table 2. The compound N,N-bis(2-aminoethyl)-N'-cyclopentadecyl-1,2-ethanediamine administered at 150 mg/kg/day is about five times more potent than colestipol hydrochloride; the effect of 150 mg/kg/day of N,N-bis(2-aminoethyl)-N'-cyclopentadecyl-1,2-ethanediamine was about half-way between the effects of 500 and 1000 mg/kg/day of colestipol hydrochloride. Also shown in Table 2 are the results using N,N-bis[2-(cyclododecylamino)ethyl]-1,2-ethanediamine This compound is about eight times more potent than colestipol. hydrochloride; the effect of 60 mg/kg/day of N,N-bis[2-(cyclododecylamino)ethyl]-1,2-ethanediamine is very similar to the effect of 500 mg/kg/day of colestipol hydrochloride.

In hyperlipidemic patients with serum cholesterol values above 200 mg per 100 ml, the compounds used to practice the present invention lower cholesterol levels when the dose of the active ingredient varies from about 0.5 to about 5 gm, administered from one to three times daily.

The preferred compounds of the present invention are:

N,N-Bis(2-aminoethyl)-N'-cyclopentadecyl-1,2-ethanediamine;

N,N-Bis-2-(cyclododecylamino)ethyl-1,2-ethanediamine;

N,N-Bis(2-aminoethyl)-N'-cyclododecyl-1,2-ethanediamine;

N'-Cyclododecyl-N,N-bis-2-(cyclododecylamino)ethyl-1,2-ethanediamine; and

N,N-Bis(2-aminoethyl)-N'-hexadecyl-1,2-ethanediamine.

The following compounds of the present invention are useful as intermediates:

N,N-Bis(2-aminoethyl)-N'-cyclohexyl-1,2-Ethanediamine;

N,N-Bis(2-aminoethyl)-N'-1,4-dioxaspiro-4,5-dec-8-yl-1,2-ethanediamine;

N,N-Bis-2 -(1,4-dioxaspiro-4,5-dec-8-ylamino)ethyl-1,2-ethanediamine;

N,N-Bis-(2-aminoethyl)-N'-phenylmethyl-1,2-ethanediamine;

N-(2-aminoethyl)-N'-(phenylmethyl)-N-(2((phenylmethyl)amino)-ethyl-1,2-ethanediamine; and N[2E-bis(2-aminoethyl)amino]ethyl]benzamide.

Without further elaboration, it is believed that one skilled in the art can, using the preceding description, practice the present invention to its fullest extent. The following detailed examples describe how to prepare the various compositions of this invention and are to be construed as merely illustrative and not limitations of the preceding disclosure in any way whatsoever.

EXAMPLE 1

Capsule

One thousand two-piece hard gelatin capsules for oral use, each containing 500 mg of N,N-bis(2-cyclododecylamino)ethyl-1,2-ethanediamine are prepared from the following ingredients:

| | |
|---|---|
| N,N-bis(2-cyclododecylamino)ethyl-1,2-ethanediamine | 500 gm |
| Talc, USP | 50 gm |
| Magnesium stearate, USP | 2 gm |

The finely powdered ingredients are mixed thoroughly, then filled into hard gelatin capsules of appropriate size. Two capsules are taken four times a day with meals and an evening snack to lower blood cholesterol in hypercholesterolemic patients.

EXAMPLE 2

Powder Packets

Ten thousand powder packets, each containing 1.25 gm of N,N-bis(2-cyclododecylamino)ethyl-1,2-ethanediamine hydrochloride are prepared from the following:

| | |
|---|---|
| N,N-bis(2-cyclododecylamino)ethyl-1,2-ethanediamine hydrochloride | 12,500 gm |

One or two packets emptied and stirred into water, fruit or vegetable juices, skimmed milk, or mixed with cereal applesauce or other food, is given four times daily.

EXAMPLE 3

Oil Base Suspension

One thousand ml of an oral suspension containing 750 mg of N,N-bis(2-cyclododecylamino)ethyl-1,2-ethanediamine in each 5 ml is prepared from the following ingredients:

| | |
|---|---|
| N,N-bis(2-cyclododecylamino)ethyl-1,2-ethanediamine | 150 gm |
| Oil base, qs | 1,000 ml |

The oil base consists of equal parts of soybean oil and purified linseed oil gelled with 1% aluminum monostearate. Each 5 ml of base supplies 1.1 ml of linolenic acid. One or two teaspoonsful (5 or 10 ml) is administered three times a day with meals.

EXAMPLE 4

Aqueous Dispersion

An aqueous oral dispersion containing in each tablespoon (15 ml) 1000 mg of N,N-bis(2-cyclododecylamino)ethyl-1,2-ethanediamine is prepared from the following materials:

| | |
|---|---|
| N,N-bis(2-cyclododecylamino)ethyl-1,2-ethanediamine | 1,000 gm |
| Pectin, NF | 100 gm |
| Deionized water, qs | 15,000 ml |

One tablespoon (15 ml) is given three times a day, with meals, to lower blood cholesterol in hypercholesterolemic individuals.

EXAMPLE 5

Powder Packets

Five thousand powder packets, each containing 2.5 gm of N,N-bis(2-cyclododecylamino)ethyl-1,2-ethanediamine hydrochloride, are prepared from 12,500 gm of the compound. One packet emptied and dispersed into an aqueous vehicle such as water fruit or vegetable juice, skimmed milk, or the like is taken four times daily to reduce the serum cholesterol levels in hypercholesterolemic patients.

EXAMPLE 6

Similar tablets, capsules, powder packets, oil base suspensions and aqueous dispersions useful in reducing hypercholesterolemia are prepared using procedures analagous o those in Examples 2 through 6 utilizing the other compounds used to practice the present invention.

EXAMPLE 7

N,N-Bis(2-aminoethyl)-N'-cyclopentadecyl-1,2-ethanediamine (Formula B-3) and N,N-bis-2-(cyclopentadecylamino)ethyl-1,2-ethanediamine (Formula B-4)

Refer to Chart B (Scheme 1)

Amine B-2 (39.1 g), methanol (800 ml), acetic acid (62 ml, and cyclopentadecanone B-1 (50.0 g) are combined. After 1.5 h, sodium is continued at room temperature. After 18 h the reaction is evacuated in vacuo. A solution of 10% sodium hydroxide (200 ml) is added to the solid. The aqueous portion is extracted with methylene chloride (3×400 ml) The combined organic fractions are dried, and concentrated in vacuo to 80.71 g. The crude material is chromatographed on silicon dioxide (2.5 kg) and eluted with chloroform/-methanol/ammonium hydroxide (10/4/1) to yield fraction A (23.84 g) and the first title product (38.0 g), which is similar by NMR to material prepared previously. Fraction A is rechromatographed in the same solvent system to yield the second title product (8.0 g).

Physical characteristics of the second title product are as follows:

$^1$H NMR (CDCl$_3$): δ1.22-1.70, 2.45-2.80.

$^{13}$C NMR (CDCL$_3$)ppm: 58.4, 57.3, 54.9, 45.5, 32.9, 27.6, 26.9, 26.8, 26.64, 26.57, 23.7.

IR (neat): 3299, 2929, 1460, 1365 cm$^{-1}$.

Chemical Ionization (NH$_3$) MS for C$_{36}$H$_{74}$N$_4$: 562, 324, 312, 251, 238.

Anal. Found: C. 76.61; H, 13.42; N, 9.87.

EXAMPLE 8

N,N-Bis(2-aminoethyl)-N'-cyclododecyl-1,2-ethanediamine (Formula B-6)

Refer to Chart B (Scheme 2)

Amine B-2 (8.2 g), methanol (100 ml), acetic acid (26 ml), and ketone B-5 (5.1 g) are combined and the pH is measured at 5. After 2 h, sodium cyano-borohydride (1.85 g) is added and the reaction is continued at room temperature. After 24 h the reaction is evaporated in vacuo. To the solid is added 10% sodium hydroxide (25 mL), pH=8. Additional sodium hydroxide is added. The aqueous portion is extracted with chloroform (3×100 ml). The combined organic fractions are extracted with 10% sodium hydroxide, dried, and concentrated in vacuo. The crude material is chromatographed on silicon dioxide (300 g) and eluted with chloroform-/methanol/ammonium hydroxide (10/4/1) to yield 6.9 g of material contaminated with solvent. Bulb to bulb distillation of the crude material in a Kugelrohr apparatus affords the title product (4.74 g).

Physical characteristics are as follows:

Bp: 180°-200° C. at 0.08 mm.

$^1$H NMR (CDCl$_3$): δ 1.22-1.60, 2.47-2.70.

$^{13}$C NMR (CDCl$_3$) ppm: 57.9, 55.3, 54.9, 45.5, 40.0, 29.4, 25.0, 24.5, 23.1, 23.0, 20.9.

IR (neat): 3363, 3283, 2932, 1658, 1470, 1446, 1347 cm$^{-1}$.

MS for $C_{18}H_{40}N_4$, (m/e): 313, 282, 278, 209, 196, 116, 99, 87.

Anal. Found: C, 69.06; H, 13.06; N, 17.93.

EXAMPLE 9

N,N-Bis-2-(cyclododecylamino)ethyl-1,2-ethanediamine (Formula B-7)

Refer to Chart B (Scheme 2)

Amine B-2 (18.28 g, methanol (900 ml), acetic acid (60 ml), and ketone B-5 (45.9 g) are combined and the pH of the reaction is between 5 and 6. After 0.5 h, sodium cyano-borohydride (16.65 g) is added portion-wise over 20 min and the reaction is continued at room temperature. After 19 h the reaction is evacuated in vacuo. A solution of 20% sodium hydroxide is added to the solid to bring the mixture to pH=12. The aqueous portion is extracted with chloroform (4×250 ml). The combined organic fractions are concentrated in vacuo. The crude material is chromatographed on silicon dioxide (2 kg) and eluted with chloroform/methanol (1/1) followed by chloroform/methanol/ammonium hydroxide (10/4/0.5), and finally with a solvent ratio of 10:4:1 to yield B-8 (14.34 g), a mixture of B-8 and B-7 (243.8 g). B-7 (8.49 g), followed by B-6 (9.05 g). The mixture of B-7 and B-8 is rechromatographed to yield B-8 (3 g), a mixed fraction (5.1 g). and B-7 (15.9 g). The large fraction of B-7 is dissolved in hexane, filtered, and evaporated in vacuo.

Physical characteristics are as follows:

$^1$H NMR (CDCl$_3$): δ 1.22-1.60, 2.47-2.70.

IR (neat): 3357, 3293, 2931, 1470, 1444 cm$^{-1}$.

MS for $C_{30}H_{62}N_4$, (m/e): 448, 282, 270, 209, 196, 99.

Chemical Ionization MS for $C_{30}H_{62}N_4$: 479.

Anal. Found: C, 75.26; H. 13.17; N, 11.74.

EXAMPLE 10

N-(2-aminoethyl)-N'-cyclododecyl-1,2-ethanediamine (Formula B-10)

Refer to Chart B (Scheme 3)

Amine B-9 (5.76 g, methanol (100 ml), acetic acid (26 ml), and ketone B-5 (5.1 g) are combined and the pH is measured at 4. After 2 h, sodium cyano-borohydride (1.85 g) is added and the reaction is continued at room temperature. After 24 h the reaction is quenched with 10% sodium hydroxide (25 ml), pH=8, and additional sodium hydroxide is added to bring the pH of the mixture to 12. The aqueous portion is extracted with chloroform (3×100 ml). The combined organic fractions are extracted with 10% sodium hydroxide, dried, and concentrated in vacuo. The crude material is chromatographed on silicon dioxide (300 g) and eluted with chloroform/methanol/ammonium hydroxide (10/4/1) to yield 5.2 g of material contaminated with solvent. Bulb to bulb distillation of the product in a Kugelrohr apparatus affords the title product (4.57 g).

Physical characteristics are as follows:

Bp: 160°-180° C. at 0.08 mm.

$^1$H NMR (CDCl$_3$): δ 1.20-1.60, 2.51-2.81.

$^{13}$C NMR (CDCl$_3$) ppm: 54.8, 52.6, 49.8, 47.0, 41.9, 29.5, 24.9, 24.4, 23.2, 23.1, 20.9.

IR (neat): 3295, 2931, 1657, 1470, 1445, 1346, 1116 cm$^{-1}$.

MS for $C_{16}H_{35}N_3$, (m/e): 270, 252, 239, 209, 197, 196, 182, 73.

Anal. Found: C. 71.07; H, 13.15; N. 15.51.

Example 11

N'-Cyclododecyl-N,N-bis-2-(cyclododecylamino)ethyl-1,2-ethanediamine (Formula B-8)

Refer to Chart B (Scheme 2)

Amine B-2 (18.28 g), methanol (900 ml), acetic acid (60 ml), and ketone B-5 (91.15 g) are combined. After 0.5 h, sodium cyanoborohydride (31.4 g) is added via Gooch tubing over several hours. The reaction is continued at room temperature for 18 h. The mixture is concentrated in vacuo and 20% sodium hydroxide (200 m) is added. The aqueous portion is extracted with hexane (3×200 ml) and the organic portions are combined and concentrated to 40.9 g. The aqueous portion is then extracted with chloroform (3×200 ml) and the organic fractions are combined and concentrated to 69.4 g. Since the TLC of both organic fractions shows a mixture of compounds, the material is combined and chromatographed on 2.5 kg of silicon dioxide eluting first with chloroform/methanol followed by chloroform/methanol/ammonium hydroxide (10/4/1). The first compound eluted is identified as cyclododecanol (21.98 g). The second compound eluted is B-8 (66.9 g). The material is heated in a Kugelrohr oven (up to 100° C. at 0.1 mm) to remove solvent and the material upon cooling slowly solidifies yielding 59.01 g of the title product.

Physical characteristics are as follows:

$^1$H NMR (CDCl$_3$): δ 1.24-1.60, 1.70, 2.51-2.70.

$^{13}$C NMR (CDCl$_3$) ppm: 55.3, 54.8, 45.2, 29.0, 25.1, 24.6, 22.9, 22.8, 20.6.

IR (mineral oil mull): 3298, 2970, 1475, 1445, 1377, 1348, 1125, 1120, 1061, 793, 774, 741, 721 cm.$^{-1}$.

MS for $C_{42}H_{84}N_4$, (m/e): 643, 448, 436, 253, 196.

Anal. Found: C. 77.83; H, 12.77; N, 8.70. Corrected for 0.22% water.

EXAMPLE 12

N,N-Bis(2-aminoethyl)-N'-cyclohexyl-1,2-Ethanediamine (Formula B-12)

Refer to Chart B (Scheme 4)

The amine B-2 (14.9 g, 15.5 ml), methanol (184 ml), acetic acid (48 ml) and cyclohexanone B-11 (5.0 g, 5.3 ml) are added to a 500 ml flask in the order given above. The solution is stirred for 45 min, and sodium cyanoborohydride (3.2 g) is added portion-wise. The solution is stirred overnight and then concentrated in vacuo. A solution of 20% sodium hydroxide is added to bring the residue to pH 12. Chloroform (45 ml) is also added to dissolve the solids. The organic layer is removed, and the aqueous layer is extracted with chloroform (3×40 ml). The organic layers are combined, dried with magnesium sulfate, filtered and concentrated in vacuo. The residue is chromatographed eluting with chloroform/methanol/ammonium hydroxide, 10/4/1. The appropriate fractions are combined and concentrated in vacuo. The residue (9.523 g) is distilled bulb to bulb (b$_{0.95}$ 155°-165° C.), yielding the title product (6.75 g) as a colorless liquid.

Physical characteristics are as follows:

$^1$H NMR (CDCl$_3$): δ 1.00-1.30, 1.41, 1.63, 1.74, 1.89, 2.35-2.45, 2.47-2.61, 2.67-2.79.

$^{13}$C NMR (CDCl$_3$) ppm: 57.2, 56.8, 54.3, 44.04, 39.5, 33.3, 25.8, 24.8; IR (neat) 3356, 3281, 2927, 2852, 1641, 1587, 1463, 1451 cm$^{-1}$.

MS for $C_{12}H_{28}N_4$, (m/e): 229, 198, 194, 181, 167, 126, 116, 99.

Anal. Found: C, 61.52; H, 12.63; N, 23.71. Water analysis: 5.52%.

EXAMPLE 13

N'-Cyclohexyl-N,N-bis[(2-cyclohexylamino)ethyl]1,2,-ethanediamine (Formula B-13).

Refer to Chart B (Scheme 4)

Amine B-2 (3.7 ml), methanol (180 ml), acetic acid (12 ml) and cyclohexanone B-11 (10.3 ml) are combined and stirred at room temperature for 0.5 h. Sodium cyanoborohydride (6.2 g) is added and the reaction is stirred at room temperature overnight. The solution is concentrated in vacuo. The residue is taken up in water (100 ml) and adjusted to pH 12 with 20% sodium hydroxide. The solution is then extracted with chloroform (3×40 ml). The organic layers are combined, dried with magnesium sulfate, filtered and concentrated in vacuo. The residue is chromatographed eluting with chloroform, ethyl-1,2-ethanediamine (Formula B-16). Refer to Chart B (Scheme 5).

Amine B-2 (37.44 g) and methanol (480 ml) are cooled in an ice bath during the addition of acetic acid (118.4 ml). Ketone B-14 (20.0 g) is then added and the reaction is stirred 0.5 h. Via Gooch tubing, sodium cyano-borohydride (8.32 g) is added portionwise. After 21 h the reaction is concentrated in vacuo. The solid is dissolved in enough 20% sodium hydroxide (-120 mL) to bring the pH to 7. The aqueous portion is extracted with chloroform (3×100 ml) and the organic portion is concentrated in vacuo to 22.0 g. This is chromatographed on silicon dioxide (700 g) and eluted with chloroform/methanol/ammonium hydroxide (10/4/1) to yield the title product (7.2 g).

Physical characteristics are as follows:

$^1$H NMR (CDCl$_3$): δ 1.37–2.00, 1.93, 2.48–2.82, 3.93.

IR (neat): 3361, 3290, 3220, 2940, 2883, 2813, 1461, 1447, 1377, 1104, 1035, 922 cm$^{-1}$.

MS for $C_{22}H_{42}N_4O_4$, (m/e): 396, 256, 244, 184, 170.

Chemical Ionization (ammonia) MS for $C_{22}H_{42}N_4O_4$: 427.

EXAMPLE 16

N,N-Bis(2-aminoethyl)-N'-cyclohexadecyl-1,2-ethanediamine (Formula B-18)

Refer to Chart B (Scheme 6)

The ketone B-17 (6.7 ml), toluene (435 ml), amine B-2 (13.0 ml) and p-toluenesulfonic acid (1.1 g) are combined and heated to reflux. The solution is heated at reflux with azeotropic removal of water for 36 h. The solution is concentrated in vacuo. The residue is taken up in absolute ethanol (200 ml) and hydrogenated over 10% Pd/C (2.0 g) at 50 psi for 2 d. The reaction mixture is filtered through a celite pad, and the pad is washed with ether. The filtrate is concentrated in vacuo and the residue is chromatographed eluting with chloroform-/methanol/ammonium hydroxide, 10/4/1. The appropriate fractions are combined and concentrated in vacuo yielding a pale green oil. Solvent traces are removed under high vacuum yielding the title product (3.1 g).

Physical characteristics are as follows:

$^1$H NMR (CDCl$_3$): δ 1.31, 1.39–1.48, 2.15, 2.57, 2.61–2.69, 2.77.

$^{13}$C NMR (CDCl$_3$) ppm: 57.3, 56.9, 54.5, 45.1, 39.7, 32.2, 27.3, 26.9, 26.4, 26.2, 23.5. followed by chloroform-/methanol (5/2) and finally with chloroform/methanol-/ammonium hydroxide (10/4/1). The appropriate fractions are combined and concentrated in vacuo producing an orange oil which is then distilled bulb to bulb yielding pure title product (6.0 g).

Physical characteristics are as follows:

b$_{0.40\ mm}$: 205°–215° C.

$^1$H NMR (CDCl$_3$): δ 1.00–1.32, 1.60–1.64, 1.71–1.75, 1.85–1.89, 2.36–2.45, 2.54–2.58, 2.66–2.73.

$^{13}$C NMR (CDCl$_3$) ppm: 57.0, 54.6, 44.6, 33.5, 26.0, 24.9.

IR (neat): 3294, 2928, 2853, 1676, 1450, 1132 cm$^{-1}$.

MS for $C_{24}H_{48}N_4$ (m/e): 393, 292, 291, 280, 268, 208, 194, 181, 167, 126, 112.

Anal. Found: C, 73.31; H, 12.22; N, 14.11. Corrected for 1.25% water.

EXAMPLE 14

N,N-Bis(2-aminoethyl)-N'-1,4,-dioxaspiro-4.5-dec8-yl-1,2-ethanediamine (Formula B-15)

Refer to Chart B (Scheme 5)

Amine B-2 (37.44 g) and methanol (480 ml) are cooled in an ice bath during the addition of acetic acid (118.4 ml). Ketone B-14 (20.0 g) is then added and the reaction is stirred 0.5 h. Via Gooch tubing, sodium cyano-borohydride (8.32 g) is added portionwise. After 23 h the reaction is concentrated in vacuo to 130 g of solid. The solid is dissolved in 20% sodium hydroxide (180 ml) and chloroform. The aqueous portion was exhaustively extracted with chloroform (>1000 ml) until little product can be detected in the aqueous layer by TLC. The organic portion is concentrated in vacuo to 36.64 g. This is chromatographed on silicon dioxide (1.5 kg) and eluted with chloroform/methanol/ammonium hydroxide, 10/4/1 to afford impure B-16 (7.1 g) and the title product, (21.9 g).

Physical characteristics are as follows:

$^1$H NMR (CDCl$_3$): δ 1.40–2.03, 2.50–2.89, 3.81, 3.93.

$^{13}$C NMR (CDCl$_3$) ppm: 164.2, 108.4, 64.2, 64.1, 56.1, 55.3, 54.0, 44.5, 39.1, 32.9, 29.7.

IR (neat): 3408, 3350, 3279, 3186, 2941, 2883, 2864, 2819, 2325, 1578, 1467, 1448, 1378, 1104, 1034, 923 cm$^{-1}$.

MS for $C_{14}H_{30}N_4O_2$, (m/e): 256, 252, 239, 184, 170, 141, 116, 99, 87.

EXAMPLE 15

N,N-Bis-2-(1.4-dioxaspiro-4.5-dec-8 -ylamino)-

IR (neat): 3357, 3286, 2929, 2857, 1640, 1461 cm$^{-1}$.

HI RES MS for $C_{22}H_{48}N_4$ Found: 369.3940; m/e: 369, 368, 350, 338, 266, 252, 116, 99, 44).

EXAMPLE 17

12-[N',N'-bis(2-aminoethyl)-N-1,2-ethanediaminyl]octadecylamide (Formula B-20)

Refer to Chart B (Scheme 7)

The amide B-19 (4.9 g) is added to a stirred solution of the amine B-2 (5.0 ml) and acetic acid (15.8 ml) in methanol (60 ml). The resulting yellow suspension is stirred at room temperature for 1 h. Sodium cyanoborohydride (1.5 g) is added portionwise and the solution is stirred overnight at room temperature. The solution is concentrated in vacuo, and the residue is taken up in water (a small amount of chloroform is added to dissolve material that does not dissolve in water). The solution is adjusted to pH 12 with 20% sodium hydroxide. The organic layer is removed, and the aqueous layer is extracted with chloroform (3×125 ml). The organic layers are combined, dried with magnesium sulfate, filtered and concentrated in vacuo. The residue is chromatographed (silicon dioxide) eluting with chloroform/methanol/ammonium hydroxide (10/4/1). The appropriate fractions are combined and concentrated in vacuo. Solvent traces are removed under high vacuum yielding the title product (3.96 g) as an orange-brown oil.

Physical characteristics are as follows:

$^1$H NMR (CDCl$_3$): δ 0.88, 1.27, 1.29–1.38, 1.63, 1.90, 2.22, 2.46, 2.53, 2.61–2.66, 2.77, 5.74.

$^{13}$C NMR (CDCl$_3$) ppm: 176.0, 57.9, 56.6, 54.0, 44.6, 39.5, 35.7, 33.2, 31.7, 29.7, 29.4, 29.3, 29.0, 25.6, 25.4, 22.5, 13.9.

IR (neat): 3355, 3300, 2925, 2853, 1672, 1625, 1466 cm$^{-1}$.

HI RES MS for C$_{24}$H$_{53}$N$_5$O, Found: 428.4315; m/e: 428, 427, 411, 385, 366, 355, 339, 327, 313, 299.

EXAMPLE 18

Methyl 14-[N′,N′-bis(2-aminoethyl)-N-1,2-ethanediaminyl-]eicosanoate (Formula B-22)

Refer to Chart B (Scheme 8)

The ketone B-21 (5.0 g) is added to a stirred solution of the amine B-2 (4.4 ml) and acetic acid (13.8 ml) in methanol (52.5 ml). The resulting yellow suspension is stirred at room temperature for 1 h. Sodium cyanoborohydride (0.925 g) is added portionwise and the solution is stirred overnight at room temperature. The solution is concentrated in vacuo. The residue is taken up in water (a small amount of chloroform is added to dissolve material that does not dissolve in water) and adjusted to pH 12 with 20% sodium hydroxide. The organic layer is removed, and the aqueous layer is extracted with chloroform (3×125 ml). The organic layers are combined, dried with magnesium sulfate, filtered and concentrated in vacuo. The residue is chromatographed (silicon dioxide) eluting with chloroform/methanol/ammonium hydroxide (10/4/1). The appropriate fractions are combined and concentrated in vacuo. Solvent traces are removed under high vacuum producing the very viscous, green oily title product (3.38 g).

Physical characteristics are as follows:

$^1$H NMR (CDCl$_3$): δ 0.88, 1.26, 1.38, 1.55–1.68, 2.10, 2.30, 2.41–2.49, 2.52, 2.59–2.65, 2.77, 3.67.

$^{13}$C NMR (CDCl$_3$) ppm: 174.0, 58.0, 54.5, 45.0, 39.5, 36.5, 36.0, 34.0, 31.9, 29.7, 25.8, 22.7, 14.1.

IR (neat): 3286, 2925, 2926, 2854, 1742, 1650, 1552, 1466 cm$^{-1}$.

HI RES MS for C$_{27}$H$_{58}$N$_4$O$_2$, Found: 471.4603; m/e: 471, 439, 408, 354, 336, 140, 85, 69, 55, 44.

EXAMPLE 19

N,N-Bis(2-aminoethyl)-N′-hexadecyl-1,2-ethanediamine (Formula C-3: wherein R$_1$ is CH$_3$-(CH$_2$)$_{14}$-)

Refer to Chart C

The amine C-2 (3.7 ml), toluene (123 ml), and aldehyde C-1 (wherein R$_1$ is CH$_3$—(CH$_2$)14—) (3.0 g), are combined in a 250 ml flask and stirred over molecular sieves for 3 d. The reaction mixture is filtered and the filtrate concentrated in vacuo producing a green residue. An NMR spectrum of this residue reveals that the aldehyde is no longer present. The green residue (6.04 g) is dissolved in ethanol (125 ml) and hydrogenated over 10% Pd/C (0.60 g) at 50 psi overnight. The reaction mixture is filtered through a celite pad, and the pad is washed several times with diethyl ether. The filtrate is concentrated in vacuo producing a yellow oil (5.86 g). The residue is chromatographed eluting with chloroform/methanol/ammonium hydroxide, 10/4/1. The appropriate fractions are combined and concentrated in vacuo yielding the product as an off-white foam. Solvent traces are removed under high vacuum affording the title product (1.13 g).

Physical characteristics are as follows:

$^1$H NMR (CDCl$_3$): δ 0.89, 1.28, 1.45–1.55, 1.92, 2.52, 2.59–2.66, 2.68–2.75, 2.79.

13C NMR (CDCl$_3$) ppm: 57.3, 54.1, 50.0, 47.6, 39.7, 31.9, 30.0, 29.7, 29.3, 27.4, 22.7, 14.1.

IR (mineral oil mull): 3408, 3282, 2739, 1572, 1366, 1307 cm$^{-1}$.

MS (m/e): 370, 340, 323, 309, 268, 254, 116, 99.

Anal Found: C, 71,61; H, 13.59; N, 15.08 (corrected for 2.33% water).

EXAMPLE 20

N,N-bis(2-aminoethyl)-N′-octyl-1,2-ethanediamine (Formula C-2: wherein R$_1$ is CH$_3$-(CH$_2$)$_6$-)

Refer to Chart C

Octanal C-1 (wherein R$_1$ is CH$_3$-(CH$_2$)$_6$-) (5.0 g), amine C-2 (11.7 ml) and p-toluenesulfonic acid (0.5 g) are dissolved in toluene (400 ml) and heated to reflux with azeotropic removal of water for 18 h. The solution is cooled to room temperature and concentrated in vacuo. The residue is dissolved in absolute ethanol (200 ml) and hydrogenated over 10% Pd/C at 50 psi for 48 h. The reaction mixture is filtered through a Celite pad, and the pad is washed with diethyl ether. The filtrated is concentrated in vacuo producing a yellow residue. The residue is chromatographed eluting with chloroform/methanol/ammonium hydroxide, 10/4/1. The appropriate fractions are combined and concentrated in vacuo yielding a yellow-green oil. Solvent traces are removed under high vacuum producing the title product (2.89 g).

Physical characteristics are as follows:

$^1$H NMR (CDCl$_3$): δ 0.88, 1.27, 1.45–1.55, 2.42, 2.52–2.59, 2.61–2.64, 2.69–2.73, 2.75–2.80. 13C NMR (CDCl$_3$) ppm: 57.0, 53.9, 49.8, 47.3, 39.5, 31.7, 29.7, 29.3, 29.1, 27.2, 22.5, 13.9.

IR (neat): 3350, 3289, 2955, 2826, 1636, 1574, 1468, 1309 cm$^{-1}$.

MS (m/e): 228, 211, 156, 142, 128, 116, 99.

EXAMPLE 21

N,N-Bis-(2-aminoethyl)-N′-phenylmethyl-1,2-ethanediamine (Formula C-3: wherein R$_1$ is phenyl);
N-(2-aminoethyl)-N′-(phenylmethyl)-N-(2((phenylmethyl)amino)ethyl-1,2-ethanediamine (Formula C-4: wherein R$_1$ is phenyl)

Refer to Chart C

Benzaldehyde C-1 (wherein R$_1$ is phenyl) (5.0 g) is added to a solution of the amine C-2 (13.0 ml) in toluene (470 ml) and the resulting solution is stirred over molecular sieves for 4 d. The molecular sieves are filtered off and the filtrate concentrated in vacuo to give a green oil. The oil is dissolved in absolute ethanol and hydrogenated over 10% Pd/C at 50 psi overnight. The reaction mixture is filtered through a Celite pad, the pad washed with ether and the filtrated concentrated in vacuo. The residue is chromatographed eluting with chloroform/methanol/ammonium hydroxide, 10/4/1. The appropriate fractions are combined and concentrated in vacuo to give the first title product (6.2 g) as the major product and a small amount of the second title product (1.1 g).

Physical characteristics for the first title product are as follows:

$^1$H NMR (CDCl$_3$): δ 2.03, 2.48, 2.59, 2.67-2.75, 3.79, 7.25-7.33.

$^{13}$C NMR (CDCl$_3$) ppm: 140.0, 128.1, 127.9, 126.7, 57.0, 53.9, 53.6, 46.5, 39.3.

IR (neat): 3358, 3286, 2942, 2824, 1584, 1494, 1464, 746, 700 cm$^{-1}$.

MS for C$_{13}$H$_{24}$N$_4$, (m/e): 206, 189, 175, 148, 134, 116, 99.

Anal. Found: C, 66.11; H, 10.31; N, 23.70.

Physical characteristics for the second title product are as follows:

$^1$H NMR (CDCl$_3$): δ 2.06, 2.45, 2.57, 2.65-2.72, 3.76, 7.24-7.33.

$^{13}$C NMR (CDCl$_3$) ppm: 140.2, 128.5, 128.2, 127.0, 57.4, 54.3, 54.0, 46.9, 39.7.

IR (neat): 3294, 3243, 3197, 2941, 2819, 1642, 1602, 1494, 1453 cm$^{-1}$.

MS (m/e): 327, 296, 284, 219, 206, 189, 175, 163, 148, 134 120, 91.

Anal. Found: C, 73.69; H, 9.36; N, 17.11.

EXAMPLE 22

N,N-bis(2-aminoethyl)-N'-(2-trifluoromethyl),phenylmethyl)-1,2-ethanediamine (Formula C-3: wherein R$_1$ is O-CF$_3$-C$_6$H$_4$-)

Refer to Chart C

The amine C-2 (8.6 ml) is added to a solution of 2-trifluoromethylbenzaldehyde C-1 (wherein R$_1$ is O-CF$_3$-C$_6$H$_4$-) (5.0 g) in toluene (290 ml). p-Toluenesulfonic acid (0.50 g) is added to the resulting solution. The solution is stirred and heated at reflux with azeotropic removal of water overnight. The solution is concentrated in vacuo producing a yellow-orange residue. The residue is dissolved in absolute ethanol (95 ml) and hydrogenated over 10% Pd/C (1.3 g) at 50 psi overnight. The reaction mixture is filtered though a celite pad, the pad is washed with diethyl ether and the filtrate is concentrated in vacuo. The residue was chromatographed eluting with chloroform/methanol/ammonium hydroxide, 10/4/1. The appropriate fractions are combined and concentrated in vacuo producing a yellow oil. Solvent traces are removed under high vacuum from the title product (5.95 g).

Physical characteristics are as follows:

$^1$H NMR (CDCl$_3$): δ 2.09, 2.50, 2.61, 2.70-2.81, 3.96, 7.35, 7.54, 7.64.

$^{13}$C NMR (CDCl$_3$) ppm: 138.9, 131.9, 130.2, 128.0, 126.8, 125.7, 124.5, 57.2, 54.3, 49.7, 47.0, 39.6.

IR (neat): 3292, 3242, 2948, 2826, 1609, 1584, 1457, 1314, 1118, 1037, 772 cm$^{-1}$.

MS for C$_{14}$H$_{23}$N$_4$F$_3$ (m/e): 305, 274, 257, 243, 231, 216, 202, 182, 159, 116, 99.

Anal. Found: C, 55.48; H, 7.75; N, 18.07.

EXAMPLE 23

N,N-bis(2-aminoethyl)-N'-[2-([(1,1'-biphenyl)-4-ylmethyl]amino)ethyl]-1,2-ethanediamine (Formula C-3: wherein R$_1$ is C$_6$H$_5$-C$_6$H$_4$-)

Refer to Chart C

The amine C-2 (8.2 ml), 4-phenylbenzaldehyde C-1 (wherein R$_1$ is C$_6$H$_5$-C$_6$H$_4$) (5.0 g), and p-toluenesulfonic acid (0.5 g) are dissolved in toluene (280 ml) and heated to reflux overnight with azeotropic removal of water. The solution is cooled to room temperature and concentrated in vacuo. The residue is dissolved in absolute ethanol (90 ml) and hydrogenated over 10% Pd/C (1.3 g) at 50 psi for 3 h. The reaction mixture is filtered through a Celite pad, the pad washed with ether and the filtrated concentrated in vacuo. The residue is chromatographed (silicon dioxide) eluting with chloroform-/methanol/ammonium hydroxide, 10/4/1. The appropriate fractions are combined and concentrated in vacuo, and solvent traces are removed under high vacuum yielding the title product as a yellow oil (5.45 g).

Physical characteristics are as follows:

$^1$H NMR (CDCl$_3$): δ 2.35, 2.49, 2.59, 2.68-2.81, 3.88, 7.28-7.49, 7.53-7.59.

$^{13}$C NMR (CDCl$_3$) ppm: 140.7, 139.7, 139.2, 128.7, 128.6, 128.5, 127.0, 127.0, 126.9, 125.8, 56.8, 54.1, 53.3, 46.8, 39.6.

IR (neat): 3360, 3295, 3055, 3028, 2890, 1600, 1487, 1451 cm$^{-1}$.

HI RES MS Found: 313.2392; (m/e): 313, 312, 294, 282, 167, 127, 116.

EXAMPLE 24

N,N-bis(2-aminoethyl)-N'-N-(2[[[3,4-bis(phenylmethoxy)phenyl]methyl]amino(ethyl-1,2-ethanediamine (Formula C-3: wherein R$_1$ is (Benzyl0)$_2$C$_6$H$_3$-)

Refer to Chart C

The amine C-2 (4.2 ml), 3,4-dibenzyloxybenzaldehyde C-1 (wherein R$_1$ is (Benzyl-0,)$_2$C$_6$H$_3$-) (4.5 g), and p-toluenesulfonic acid (0.45 g) are dissolved in toluene (144 ml) and heated to reflux overnight with azeotropic removal of water. The solution is cooled to room temperature and concentrated in vacuo. The residue is taken up in a small amount of absolute ethanol (15 ml). This solution is added dropwise to a solution of sodium borohydride (2.2 g) in absolute ethanol (130 ml). The reaction is stirred for 24 h, quenched with water (90 ml) and stirred for an additional 0.5 h. The reaction mixture is extracted with chloroform (3×90 ml). The organic layers are combined dried with magnesium sulfate, filtered and concentrated in vacuo. The residue is chromatographed (silicon dioxide) eluting with chloroform-/methanol/ammonium hydroxide, 10/4/1. The appropriate fractions are combined and concentrated in vacuo yielding the title product as a green-yellow oil (1.81 g).

Physical characteristics are as follows:

$^1$H NMR (CDCl$_3$): δ 2.37, 2.47, 2.56, 2.61, 2.73, 3.69, 5.13, 5.15, 6.78-6.96, 7.26-7.45.

$^{13}$C NMR (CDCl$_3$) ppm: 149.0, 148.0, 137.3, 133.2, 129.0, 128.3, 127.6, 127.2, 127.2, 126.1, 121.1, 115.2, 115.0, 71.3, 71.1, 56.7, 53.9, 53.2, 46.5, 39.5.

IR (neat): 3472, 3446, 3357, 3286, 3063, 2934, 2821, 1605, 1590, 1511, 1454, 1424 cm$^{-1}$.

HI RES MS Found: 448.2840; (m/e): 449, 431, 418, 401, 389, 363, 345, 323, 303, 211, 181, 116, 91.

EXAMPLE 25

N'[2-Bis (2-aminoethyl)-(aminoethyl)octadecanamide (Formula D-3) and N,N'-[[(2 aminoethyl)imino)di-2,1-ethanediyl]bis-octadecanamide (Formula D-4)

Refer to Chart D (Scheme 1)

The amine D-2 (2.92 g) and methyl octadecanoate D-1 (2.98 g) are heated on a steam bath, under nitrogen, for 24 h. The resulting solid is heated in water and is then filtered to remove excess amine. The solid is chromatographed on silicon dioxide (40 g), eluting first with methanol/chloroform, followed by chloroform/methanol/ammonium hydroxide, 10/4/1. The diamide D-4 (0.66 g) elutes first followed by the amide D-3 (1.89 g).

Physical characteristics for the first title product are as follows:

$^1$H NMR (CDCl$_3$): δ 0.88, 1.25, 1.61, 2.16, 2.52–2.61, 2.78, 3.31, 7.10–7.18.

IR (mineral oil mull): 3306, 2907, 1643, 1551, 1471 cm$^{-1}$.

Physical characteristics for the second title product as are follows:

$^1$H NMR (CDCl$_3$): δ 0.88, 1.25, 1.55–1.68, 2.07, 2.52, 2.58, 2.73, 3.26–3.87, 6.71–6.80.

IR (mineral oil mull): 3297, 3079, 2919, 1637, 1557, 1467, 1367 cm$^{-1}$.

EXAMPLE 26

N[2 [-bis(2-aminoethyl)amino]ethyl]benzamide (Formula D-13); and N-N'-(((2-aminoethyl)imino)di-2,1-ethanediyl)bis-benzamide (Formula D-14)

Refer to Chart D (Scheme 5)

Benzoic anhydride (5.0 g) is dissolved in methylene chloride (250 ml) and the mixture is added dropwise to a stirred solution of the amine D-2 (6.6 ml) in methylene chloride (850 ml) over a period of 50 min. The solution is allowed to warm to room temperature and is stirred overnight. After 16 hr, a small amount of white precipitate forms. The solution is concentrated in vacuo. The residue is dissolved in water and adjusted to pH 12 with 20% sodium hydroxide. The solution is extracted with chloroform (7×100 ml). The organic layers are combined, dried with magnesium sulfate, filtered and concentrated in vacuo. The residue is chromatographed (silicon dioxide) eluting with chloroform/methanol/ammonium hydroxide, 10/4/1. The less polar fractions are combined and concentrated in vacuo to yield the bis adduct as a green oil. Solvents traces are removed under high vacuum affording the second title product (0.52 g).

Physical characteristics of the second title product are as follows:

$^1$H NMR (CDCl$_3$): δ 1.80, 2.60, 2.74–2.81, 3.55, 7.24–7.29, 7.38–7.43, 7.55, 7.70–7.73.

IR (neat): 3299, 3030, 2939, 2870, 1639, 1603, 1577, 1545, 1490, 1309, 711 cm$^{-1}$.

HI RES MS Found: 355.2134 (m/e): 355, 354, 324, 220, 191, 177, 148, 105.

The appropriate more polar fractions are combined and concentrated in vacuo. Solvent traces are removed under high vacuum yielding the first title product as a green oil, (2.27 g).

Physical characteristics of the first title product are as follows:

$^1$H NMR (CDCl$_3$): δ 1.98, 2.57, 2.70, 2.77, 3.52, 7.37–7.49, 7.84–7.90, 8.05.

$^{13}$C NMR (CDCl$_3$) ppm: 167.4, 134.6, 130.9, 128.1, 126.9, 56.6, 52.9, 39.5, 38.2.

IR (neat): 3453, 3350, 3284, 2942, 2820, 1642, 1603, 1578, 1545, 1457, 1309, 711.

HI RES MS Found: 251.1885, (m/e) 252, 251, 250, 232, 220, 208, 191.

EXAMPLE 27

N-(8-aminooctyl)-benzamide (Formula D-11) and N,N'-1.8-octanediylbis-benzamide (Formula D-12)

Refer to Chart D (Scheme 4)

A solution of benzoic anhydride D-9 (1.00 g) in methylene chloride (110 ml) is added dropwise to a vigorously stirred solution of the amine D-10 (1.27 g) in methylene chloride (330 ml) at -78° C. over a period of 45 min. The resulting suspension is allowed to stir at room temperature overnight. The reaction mixture is extracted with 5% aqueous hydrochloric acid (2×300 ml). The organic layers are combined and concentrated in vacuo producing a white solid which cannot be further purified due to its insolubility. The HCl layer is adjusted to pH 11 with ammonium hydroxide and extracted with methylene chloride (3×300 ml). The organic layers are combined and concentrated in vacuo producing an off-white solid which is chromatographed eluting with chloroform/methanol/ammonium hydroxide, 20/8/1. A small amount of the second title product (0.068 g) is isolated off the column.

Physical characteristics of the second title product are as follows:

$^1$H NMR (CDCl$_3$): δ 1.37, 1.54–1.70, 6.15, 7.43–7.49, 7.74–7.77.

IR (mull): 3323, 2953, 1631, 1532, 1489, 1476, 1083, 645, 616 cm$^{-1}$.

HI RES MS Found: 352.2135 (m/e) 352, 247, 231, 218, 204, 190, 148, 135, 105.

The subsequent fractions are combined and concentrated in vacuo yielding the white solid, (0.52 g).

Physical characteristics of the first title product are as follows:

Mp: 120°–125° C.

$^1$H NMR (CDCl$_3$): δ 1.25–1.50, 1.55–1.70, 2.68, 3.47, 6.12, 7.41–7.50, 7.76.

$^{13}$C NMR (CDCl$_3$) ppm: 167.0, 134.5, 131.0, 128.3, 126.6, 42.0, 39.8, 33.5, 29.4, 29.1, 29.0, 26.7, 26.5.

IR (mull): 3332, 2923, 1632, 1533, 1447 cm$^{-1}$.

MS (m/e): 248, 232, 219, 204, 190, 176, 162, 148, 135, 114, 105.

Anal. Found: C, 72.15; H, 10.02; N, 11.27 (corrected for 1.51% water).

EXAMPLE 28

3,3'[-2-(Cyclododecylamino)ethyl-imino-bis(2,1-ethanediylimino)]-bis-propanenitrile (Formula E-3)

Refer to Chart E (Scheme 1)

Alkyl amine E-1 (B-6 of EXAMPLE B) (5.0 g) and methanol (16 ml) are cooled in an ice bath. Acrylonitrile E-2 (2.1 ml) is added at 0.3 ml/min. After 3 hr the reaction is complete and the contents of the flask are concentrated in vacuo to 7.22 g. This is chromatographed on silicon dioxide (200 g) eluting first with methanol/chloroform, followed by chloroform/methanol/ammonium hydroxide, 10/4/1 to provide a pure fraction of the title product (4.12 g) followed by a less pure fraction (2.0 g).

Physical characteristics for the pure fraction of the title product are as follows:

$^1$H NMR (CDCl$_3$): δ 1.20–1.60, 1.72, 2.5–2.75, 2.93.

$^{13}$C NMR (CDCl$_3$) ppm: 118.7, 55.1, 54.4, 54.0, 46.7, 45.0, 29.0, 24.8, 24.2, 22.8, 22.8, 20.7, 18.5.

IR (neat): 3306, 2934, 2905, 2247, 1470, 1132, 1061 cm$^{-1}$.

MS (m/e) 335, 278, 265, 222, 196, 152, 140.

Chemical Ionization (ammonia) MS: 419.

Anal. Found: C, 68.94; H, 11.34; N, 19.86.

EXAMPLE 29

N,N'(2-(Cyclododecylamino)ethyl-imino-di-2,1-ethanediyl)-bis-1,3-propanediamine (Formula E-4)

Refer to Chart E (Scheme 1)

A solution of dinitrile, the title product of Example 28 (2.92 g) and tetrahydrofuran (5 ml) is added to a cooled (0° C.) mixture of lithium aluminum hydride (1.06 g) and tetrahydrofuran (25 ml). The reaction is warmed to room temperature and stirred for 6 hr. Ammonium chloride (20 ml) is used to quench the reaction and 20% sodium hydroxide is used to bring the mixture to pH 12. The aluminum salts are removed by filtration and the filtrate is extracted with chloroform (3×150 ml). The organic layers are combined, dried, and concentrated to provide the title product (3.3 g).

Physical characteristics of the title product are as follows:

$^1$H NMR (CDCl$_3$): δ 1.20–1.70, 2.50–2.90.

$^{13}$C NMR (CDCl$_3$) ppm: 55.1, 54.9, 54.4, 47.8, 45.6, 40.4, 33.9, 29.2, 25.0, 24.4, 22.9, 22.8, 20.7.

IR (neat heated): 3286, 2930, 1634, 1598, 1470, 1446, 1125 cm$^{-1}$.

Chemical Ionization (isobutylene) MS (m/e): 427.

EXAMPLE 30

N,N'(2-(Cylododecylamino)ethyl-imino-di-2,1-ethanediyl)-bis-betaalanine, dimethyl ester (Formula E-6)

Refer to Chart E (Scheme 2)

At 0° C. alkyl amine E-1(B-6) of Example 8 (3.12 g) methanol (10 ml), and methyl acrylate (1.8 ml), (172 g) are combined. After 1 hr the reaction has warmed to room temperature, and the reaction is continued for an additional 5 hr at room temperature. Concentration of the reaction in vacuo leaves an oil which is chromatographed on silicon dioxide (150 g) and eluted with methanol/chloroform, followed by chloroform/methanol/ammonium hydroside (10/4/1). Combination of the appropriate fractions yields the title product (3.29 g).

Physical characteristics of the title product are as follows $^1$H NMR (CDCl$_3$): δ 1.20–1.60, 2.13, 2.40–2.74, 2.88, 3.68.

$^{13}$C NMR (CDCl$_3$) ppm: 173.1, 55.2, 54.6, 54.2, 51.4, 47.3, 45.1, 45.0, 34.3, 29.0, 25.0, 24.4, 22.9, 22.85, 20.7.

IR (neat): 3306, 2934, 1739, 1663, 1470, 1443, 1438, 1196, 1177 cm$^{-1}$.

MS (m/e): 485, 453, 411, 368, 288, 276, 173.

Anal. Found: C, 64.19; H, 10.81; N, 11.76 (corrected for 1.9% water).

EXAMPLE 31

1-Amino-N-(2-aminoethyl)-10-[2-cyclododecylamino)ethyl]-4-oxo-3,7,10,13-tetraazahexadecan16-amide (Formula E-7)

Refer to Chart E (Scheme 2)

Ethylene diamine (49.4 g) is added to a solution of the title product of Example 30 (5.0 g) in methanol (105 ml). The reaction is stirred at room temperature for 4 days. The solution is concentrated in vacuo and solvent traces are removed under high vacuum producing the title product as a green oil (4.39 g).

Physical characteristics of the title product are as follows $^1$H NMR (CDCl$_3$): δ 1.35, 1.48–1.55, 1.61, 2.35–2.45, 2.59, 2.67, 2.75–2.89, 3.25–3.38, 7.80.

$^{13}$C NMR (CDCl$_3$) ppm: 172.8, 55.1, 54.7, 54.1, 47.2, 45.7, 45.0, 41.9, 41.4, 35.8, 29.2, 24.9, 24.3, 22.9, 22.8, 20.7.

EXAMPLE 32

N-Cyclododecyl-N',N'-bis-2-(dimethylamino)ethylN-methyl-1,2-ethanediamine (Formula F-3)

Refer to Chart F (Scheme 2)

The alkyl amine F-1 (B-6) of Example 8 (5.0 g) is cooled to 0° C. and formic acid (6.2 g) is added, followed by formaldehyde (9.1 g). The reaction is heated to 80° C. with vigorous evolution of gas. After continuing the reaction overnight, the material is concentrated in vacuo. The residue is brought to pH 12 with 10% sodium hydroxide. The aqueous portion is extracted with chlorofors: (3×50 ml), dried and concentrated to 6.0 g. Bulb to bulb distilled of the liquid afforded pure title product (5.29 g).

Physical characteristics of the title product are as follows:

Bp: 160°–180 ° C. at 0.1 mm.

$^1$H NMR (CDCl$_3$): δ 1.22–1.52, 2.24, 2.32–2.66.

$^{13}$C NMR (CDCl$_3$) ppm: 57.6, 57.4, 53.9, 52.9, 51.3, 45.7, 37.9, 25.3, 23.7, 23.6, 23.4, 22.4, 22.3.

IR (neat): 2938, 2907, 1691, 1469, 1265, 1123, 1042 cm$^{-1}$.

MS (m/e): 324, 224, 223, 210, 172, 160, 129, 72.

Anal. Found: C, 72.00; H, 13.22; N. 14.88.

EXAMPLE 33

2,2'-[2-(Cyclododecylmethylamino)ethyl-imino]-bis-N,N,N-trimethylethanaminium diiodide (Formula F-4)

Refer to Chart F (Scheme 2)

The title product of Example 32 (1.0 g) and acetonitrile (250 ml) are combined Methyl iodide (740 mg) in acetonitrile (1 ml) is added to the reaction After 14 hr, a white solid is present in the flask. The contents of the flask are concentrated in vacuo to yield 1.67 g of the title product.

Physical characteristics of the title product are as follows:

$^1$H NMR (CDCl$_3$): δ 1.01–1.30, 2.03, 2.30–2.42, 2.50–2.60, 2.72–2.86, 3.03, 3.24, 3.72.

$^{13}$C NMR (CDCl$_3$) ppm: 61.6, 58.0, 52.8, 51.3, 50.6, 46.7, 37.5, 24.9, 23.5, 23.4, 23.0, 22.2.

IR (mineral oil mull): 3475, 2922, 2856, 1468, 1377, 947, 918 cm$^{-1}$.

MS (m/e): 667, 539, 397, 338, 224, 58.

Anal. Found: C, 45.10; H, 8.63; N, 8.46.

EXAMPLE 34

N-bis-2-(Dimethylamino)ethyl-N-1,4-dioxaspiro4.5-dec-8-yl-N-methyl-1,2-ethanediamine (Formula F-6)

Refer to Chart F (Scheme 2).

To a flask equipped with an overhead stirrer amine F-5 is added (3.05 g) and cooled to 0° C. Formic acid (4.1 g, 95% pure) and formaldehyde (6.2 g. 36% in aq. sol.) are added. The reaction is heated to 80° C. for 22 hr with evolution of carbon dioxide. The contents of the flask are concentrated in vacuo and are then made basic (pH=12) with 20% sodium hydroxide (10 ml). The aqueous portion is extracted with chloroform (3×10 ml) and concentration of the organic portions yields 3.61 g of crude product. The crude material is bulb to bulb distilled in a kugelrohr oven to afford the title product (2.25 g).

Physical characteristics of the title product are as follows.

Bp: 160°–180° C. at 0.1 mm.

$^1$H NMR (CDCl$_3$): δ 1.50–1.66, 1.69–1.85, 2.24, 2.26, 2.35–2.68, 3.93.

IR (neat): 2943, 2816, 2766, 1463, 1106, 1033, 927 cm$^{-1}$.

MS (m/e): 298, 198, 184, 172, 129, 72.

Anal. Found: C. 63.80; H, 11.50.

FORMULAS $Z-(CH_2)_n-X_1-R_1$      Formula 1

Formula 2

CHART A $Z_1=O + H_2N-(CH_2)_m-N-(CH_2)_q-NH_2$
                                                         $(CH_2)_r$
                                                         $NH_2$

A-1        A-2

↓

$Z_1-NH-(CH_2)_m-N-(CH_2)_q-NH$ + $Z_1-NH-(CH_2)_m-N-(CH_2)_q-NHR_6$
                $(CH_2)_r$                                             $(CH_2)_r$
                $NH_2$                                                     $NH_2$

A-3        +        A-4

$Z_1-NH-(CH_2)_m-N-(CH_2)_q-NHR^6$
                                $(CH_2)_r$
                                $NHR_8$

A-5

CHART B
(Scheme 1)

=O + N(CH$_2$CH$_2$NH$_2$)$_3$

B-1        B-2

↓

-continued
CHART B
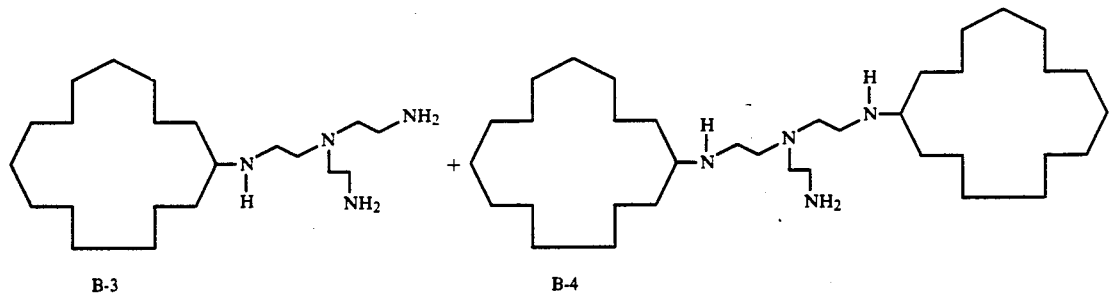
(Scheme 2)
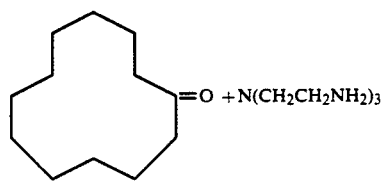
B-5  B-2
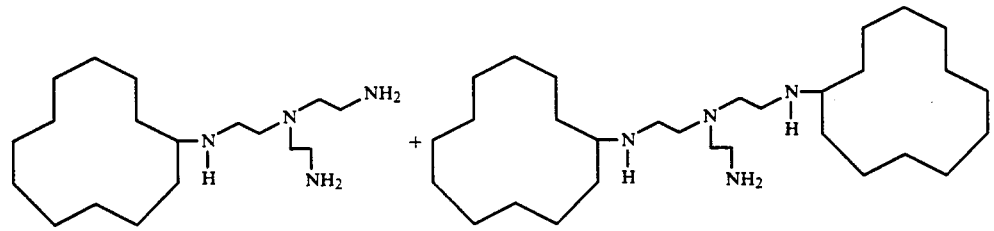
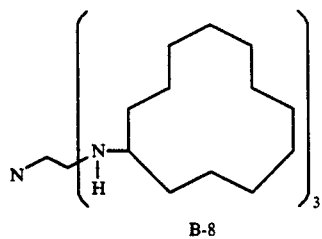
(Scheme 3)
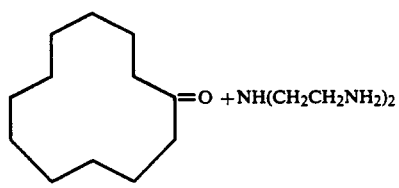
B-5  B-9

-continued
CHART B
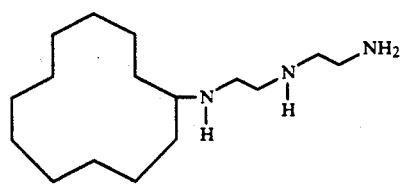
B-10
(Scheme 4)
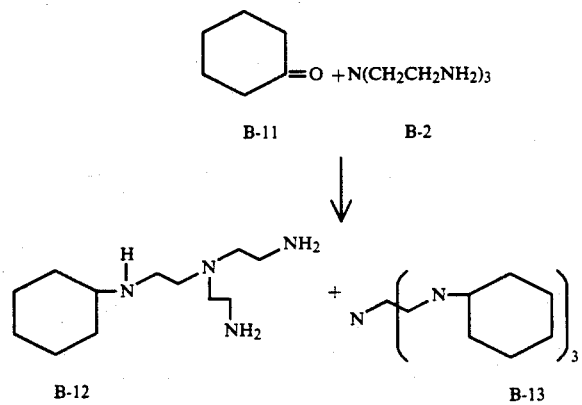
(Scheme 5)
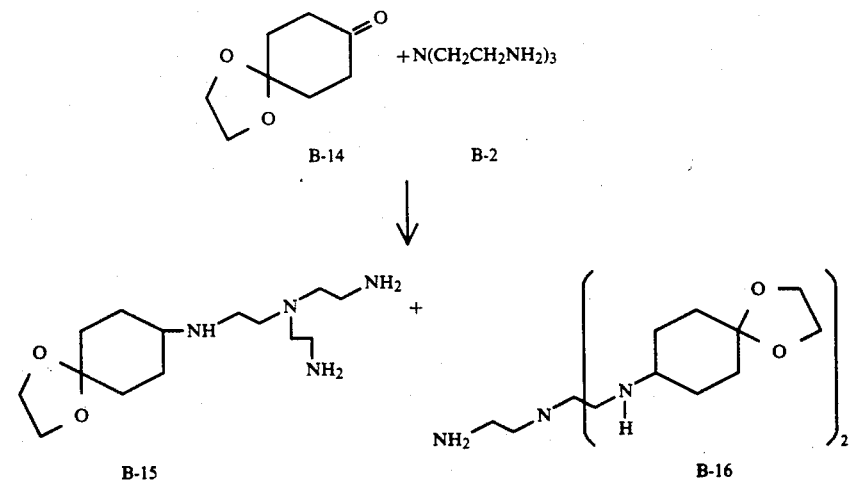
(Scheme 6)
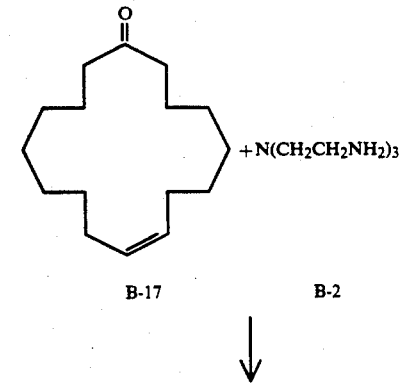

-continued
CHART B
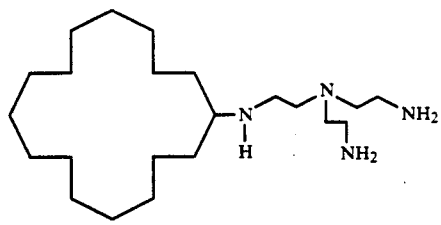
B-18
(Scheme 7)
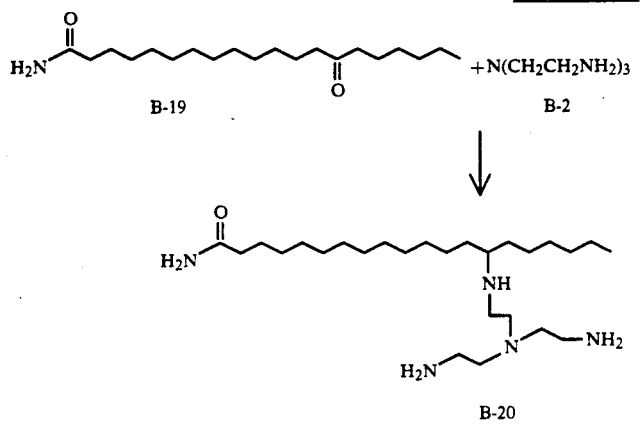
(Scheme 8)
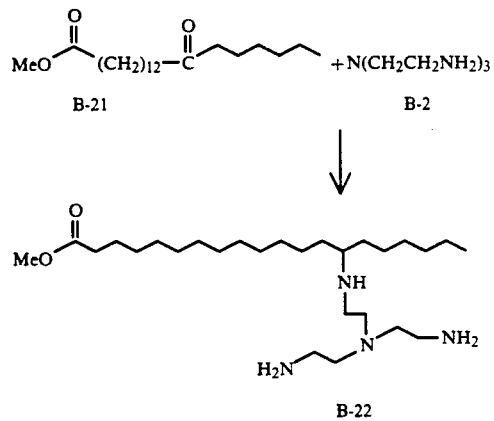
CHART C
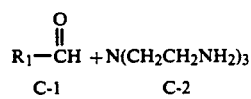
C-1    C-2
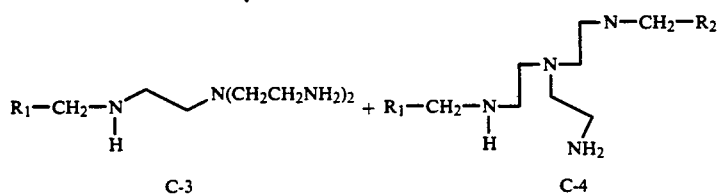
$CH_3-(CH_2)_{14}-$

CHART C
CH₃—(CH₂)₆—
C₆H₅—
phenyl-CF₃—C₆H₄—
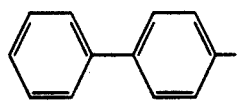
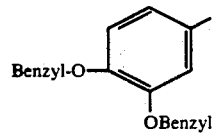
CHART D
(Scheme 1)
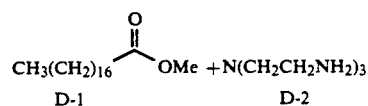
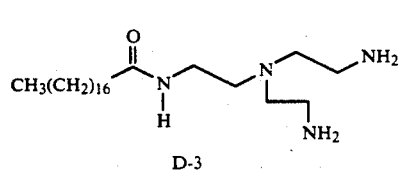        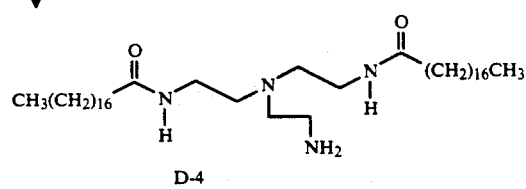
(Scheme 2)
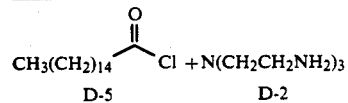
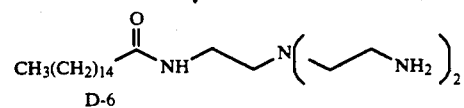
(Scheme 3)
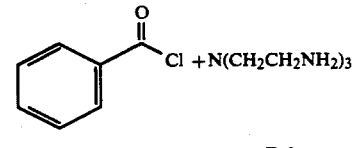
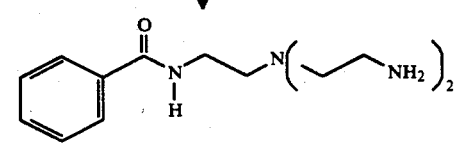
(Scheme 4)

CHART D
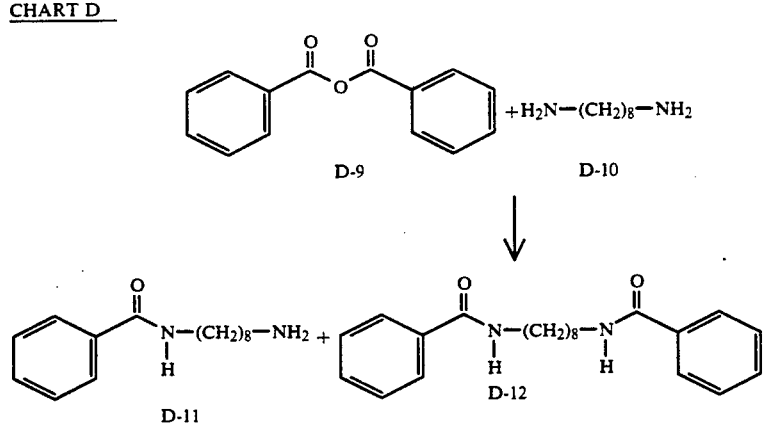
(Scheme 5)
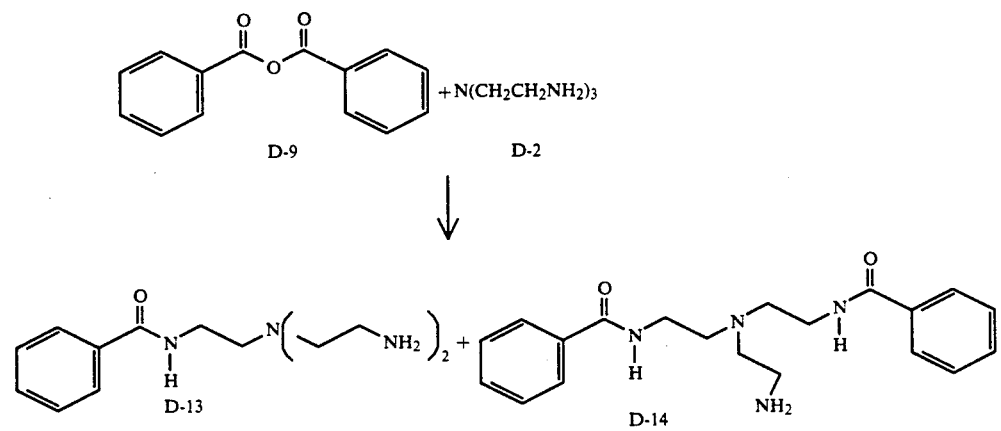
CHART E
(Scheme 1)
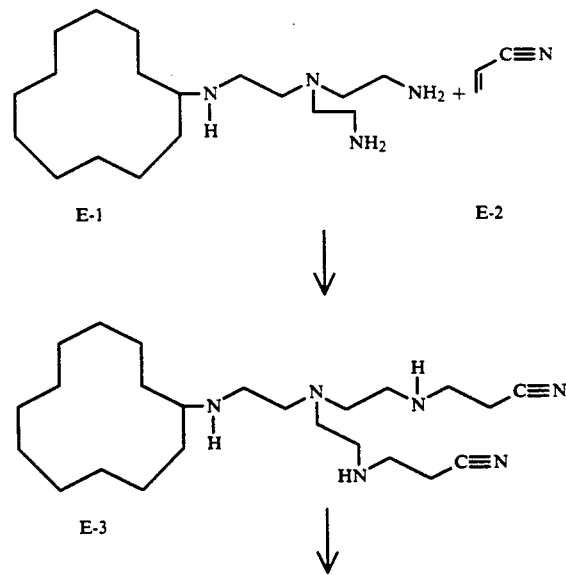

CHART E
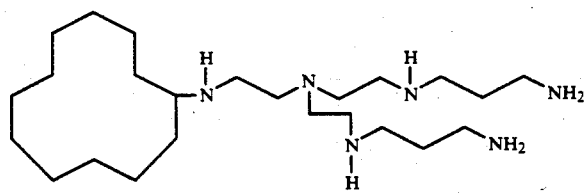
E-4
(Scheme 2)
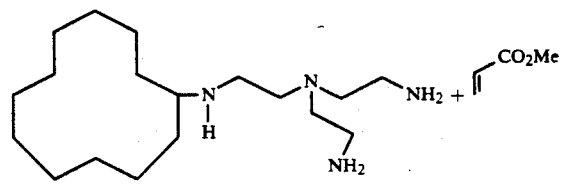
E-1 (B-6)
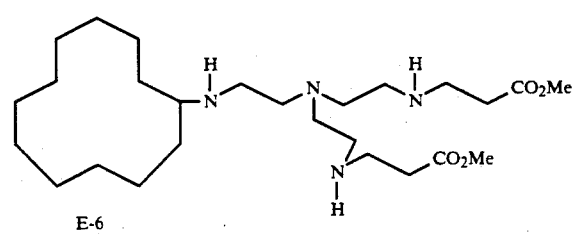
E-6
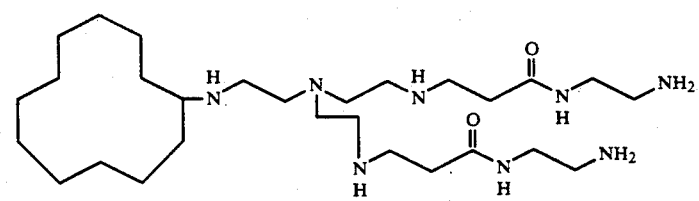
E-7
CHART F
(Scheme 1)
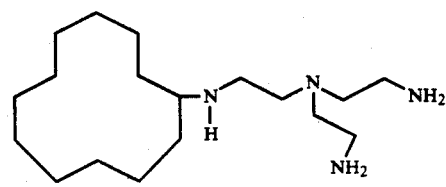
F-1 (B-6)
-continued
CHART F
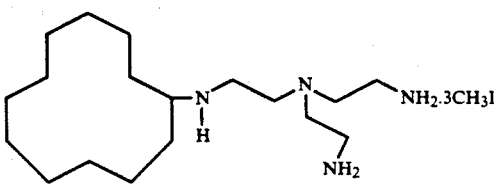
F-2
(Scheme 2)

-continued
CHART F
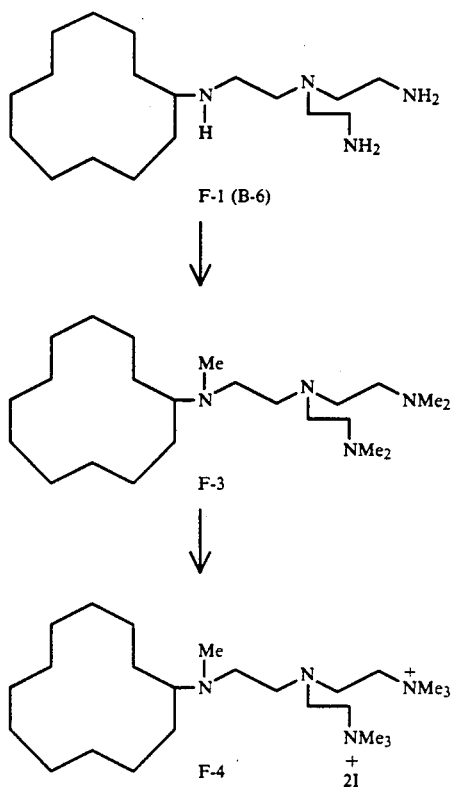
(Scheme 3)
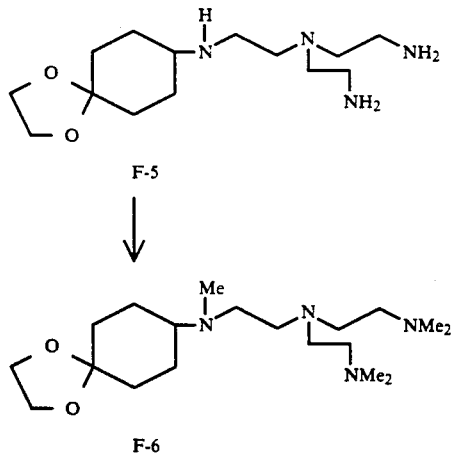
CHART G
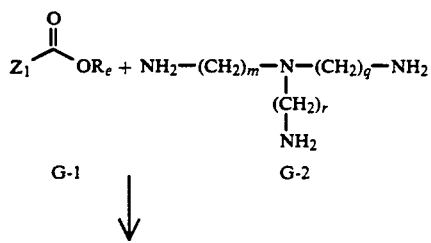
-continued
CHART G
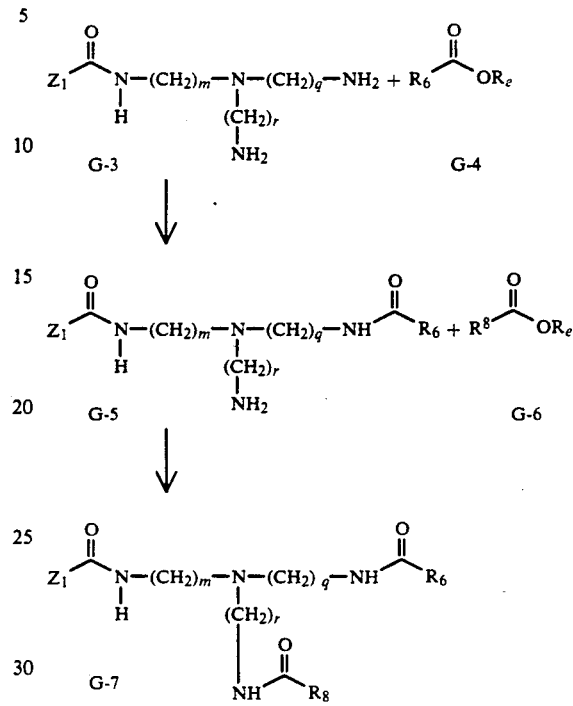
CHART H
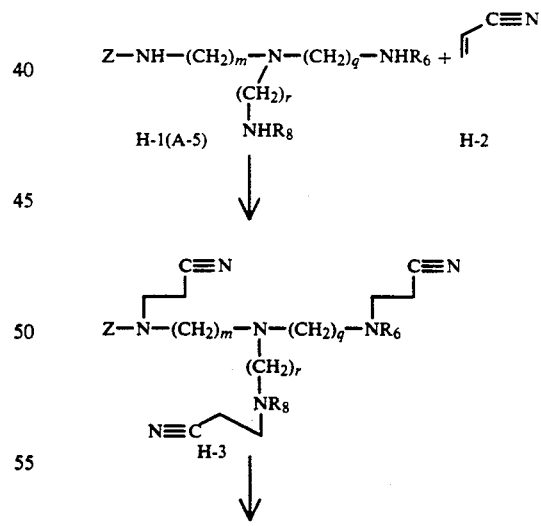

CHART I

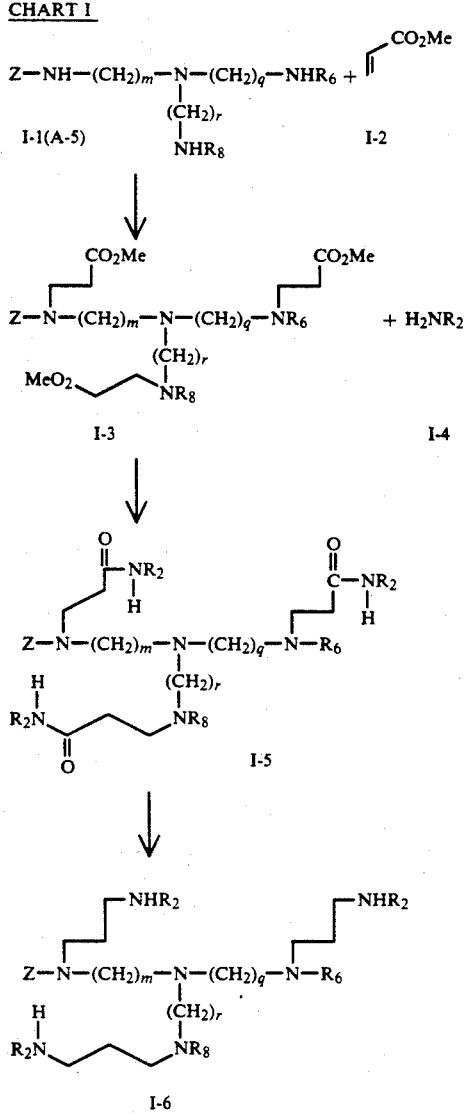

TABLE 1

Serum lipoprotein cholesterol in SEA quail fed 0.5% cholesterol-1% peanut oil: Effect of bile acid binding compounds

| Example # of Compound Tested | Dose mg/kg/ day | No. of animals | Serum Cholesterol (mg/dl) Alpha | Beta | Total |
|---|---|---|---|---|---|
| Normal Diet | — | 10 | 156 | 55 | 218 |
| Cholesterol/Peanut Oil Diet | — | 19 | 170 | 264 | 444 |
|  | — | 17 | 218 | 252 | 492 |
|  | — | 20 | 218 | 276 | 519 |
| Colestipol hydrochloride | 500 | 10 | 200 | 184 | 405 |
|  | 750 | 10 | 165 | 138** | 321* |
|  | 750 | 10 | 201 | 122* | 327 |
|  | 1000 | 10 | 210 | 129* | 366 |
|  | 2000 | 10 | 222 | 61** | 287** |
|  | 2250 | 10 | 150 | 83** | 239** |
| Example 7 (1st cpd.) | 150 | 10 | 162 | 77** | 243** |
|  | 10 | 10 | 239 | 299 | 567 |
|  | 30 | 10 | 243 | 325 | 590 |
|  | 100 | 10 | 280* | 191 | 481 |
|  | 300 | 10 | 194 | 60** | 256** |
|  | 150 | 10 | 179 | 80** | 264** |
| Example 8 | 150 | 10 | 209 | 166 | 415 |
|  | 30 | 10 | 273 | 332 | 638 |
|  | 100 | 10 | 279 | 166 | 455 |
|  | 300 | 10 | 219 | 65** | 289** |

TABLE 1-continued

Serum lipoprotein cholesterol in SEA quail fed 0.5% cholesterol-1% peanut oil: Effect of bile acid binding compounds

| Example # of Compound Tested | Dose mg/kg/ day | No. of animals | Serum Cholesterol (mg/dl) Alpha | Beta | Total |
|---|---|---|---|---|---|
|  | 200 | 10 | 205 | 116** | 326 |
| Example 10 | 150 | 10 | 187 | 240 | 440 |
| Example 7 (2nd cpd.) | 150 | 10 | 182 | 95** | 281** |
| Example 12 | 150 | 10 | 215 | 368 | 598-I |
| Example 14 | 150 | 10 | 187 | 337 | 531-I |
| Example 32 | 150 | 7 | 82** | 51** | 137** |
| Example 15 | 25 | 10 | 202 | 546 | 776-I |
| Example 9 | 25 | 10 | 215 | 172 | 407 |
|  | 150 | 10 | 162 | 85** | 251** |
|  | 10 | 10 | 192 | 263 | 483 |
|  | 25 | 10 | 211 | 322 | 555 |
|  | 50 | 10 | 202 | 135** | 347** |
|  | 100 | 10 | 176* | 70** | 247** |
| Example 33 | 150 | 10 | 224 | 144 | 379 |
| Example 19 | 100 | 10 | 213 | 142 | 361 |
| Example 11 | 25 | 10 | 203 | 301 | 511 |
|  | 50 | 9 | 209 | 216 | 438 |
|  | 100 | 10 | 224 | 131** | 368** |
|  | 10 | 10 | 193 | 235 | 441 |
| Example 29 | 150 | 10 | 206 | 130 | 354 |
| Example 22 | 50 | 10 | 222 | 212 | 455 |
| Example 21 (1st cpd.) | 150 | 10 | 203 | 327 | 562-I |
| Example 17 | 50 | 10 | 191 | 185 | 387 |
| Example 18 | 50 | 10 | 223 | 251 | 490 |
| Example 23 | 100 | 10 | 206 | 173 | 398 |
| Example 13 | 150 | 10 | 226 | 180 | 437 |

* and **significantly different from cholesterol/peanut oil diet controls
*P = 0.006
**P = 0.001
-I = inactive

TABLE 2

Serum lipoprotein cholesterol in rats fed 1% cholesterol: Effect of bile acid binding compounds

| Compound | Dose mg/kg/day | No. of animals | Serum Cholesterol (mg/dl) Alpha | Beta | Total |
|---|---|---|---|---|---|
| Normal Diet | — | 10 | 84 | 21 | 105 |
| Cholesterol Diet | — | 20 | 70 | 56 | 129 |
|  | — | 20 | 64 | 66 | 131 |
|  | — | 20 | 60 | 73 | 135 |
| Colestipol hydrochloride | 500 | 10 | 67 | 36 | 104 |
|  | 500 | 10 | 70 | 41 | 113 |
|  | 1000 | 10 | 72 | 25 | 98 |
|  | 1000 | 10 | 72 | 29 | 102 |
| N,N-bis(2-aminoethyl)-N'-cyclopentadecyl-1,2-ethanediamine | 150 | 10 | 48* | 31** | 81 |
| N,N-bis[2-cyclododecylamino)-ethyl]-1,2-ethanediamine | 3 | 10 | 57 | 93 | 155 |
|  | 10 | 10 | 57 | 76 | 135 |
|  | 30 | 10 | 58 | 58 | 125 |
|  | 60 | 10 | 39** | 43** | 84** |
|  | 100 | 10 | 45** | 53 | 102* |

* and **significantly different from cholesterol diet
*P = 0.006
**P = 0.001

We claim:
1. A compound of formula X, below,

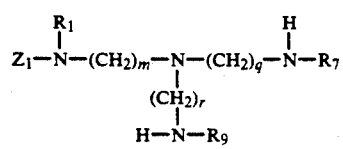

wherein $Z_1$ is (a) —$C_3$—$C_{20}$-cycloalkyl substituted with zero or one =O, —C(O)O$R_{11}$, —C(O)$NH_2$, —CH=$CH_2$, or ethylene ketal;

wherein $R_1$ is
(a) —H,
(b) —$C_1$—$C_4$alkyl;

wherein $R_7$, or $R_9$ is each independently
(a) —H,
(b) —$C_3$—$C_{20}$cycloalkyl substituted with zero or one =O, C(O)O$R_{11}$, —C(O)$NH_2$, —CH=$CH_2$, or ethylene ketal,
(c) —$C_3$—$C_{20}$alkyl substituted with one =O, —C(O)O$R_{11}$, —C(O)$NH_2$, —CH=$CH_2$, or ethylene ketal, or C≡N, provided that $R_7$ and $R_9$ are not both —H. wherein $R_{11}$ is each independently
(a) —H,
(b) —$C_1$—$C_6$alkyl, or
(c) —$(CH_2)_n$—$NH_2$;

wherein n is zero to five, inclusive;
wherein m, q, or r is each independently one to three, inclusive.

2. A compound of claim 1, wherein
$Z_1$ is —$C_6$—$C_{20}$-cycloalkyl substituted with ethylene ketal;

3. A compound of claim 1, wherein,
$Z_1$ is $C_{12}$—$C_{20}$-cycloalkyl substituted with zero or one =O, —C(O)O$R_{11}$, —C(O)$NH_2$, —CH=$CH_2$, or ethylene ketal.

4. A compound of claim 2, 1,2-Ethanediamine, N,N-bis-2-(1,4-dioxaspiro-4.5-dec-8-ylamino)ethyl-.

5. A compound of claim 3, selected from
(a) 1,2-Ethanediamine,N'-cyclohexyl-N,N-bis(2-(cyclohexylamino)ethyl)-;
(b) Propanenitrile, 3,3'-(2-(cyclododecylamino)ethylimino-bis(2,1-ethanediylimino))-bis-;
(c) .beta.-Alanine, N,N'-(2-(cyclododecylamino)ethylimino-di-2,1-ethanediyl)-bis-, dimethyl ester;
(d) 1,2-Ethanediamine, N,N-bis-2-(cyclododecylamino)ethyl-;
(e) 1,2-Ethanediamine, N'-cyclododecyl-N,N-bis-2-(cyclododecylamino)ethyl-;
(f) 1,2-Ethanediamine, N,N-bis-2-(cyclopentadecylamino)ethyl-.

6. A method of treating hypercholesterolemia in an affected patient which comprises administering to said patient an effective amount for reducing serum cholesterol in said patient of a member selected from the group consisting of the free bases and pharmaceutically acceptable salts of a compound of claim 1.

7. A method of treating hypercholesterolemia in an affected patient which comprises administering to said patient an effective amount for reducing serum cholesterol in said patient of a member selected from the group consisting of the free bases and pharmaceutically acceptable salts of a compound of claim 2.

8. A method of treating hypercholesterolemia in an affected patient which comprises administering to said patient an effective amount for reducing serum cholesterol in said patient of a member selected from the group consisting of the free bases and pharmaceutically acceptable salts of a compound of claim 3.

9. A method of treating hypercholesterolemia in an affected patient which comprises administering to said patient an effective amount for reducing serum cholesterol in said patient of a member selected from the group consisting of the free bases and pharmaceutically acceptable salts of a compound of claim 4.

10. A method of treating hypercholesterolemia in an affected patient which comprises administering to said patient an effective amount for reducing serum cholesterol in said patient of a member selected from the group consisting of the free bases and pharmaceutically acceptable salts of a compound of claim 5.

* * * * *